United States Patent
Fuchs et al.

(10) Patent No.: US 8,669,419 B2
(45) Date of Patent: Mar. 11, 2014

(54) ENGINEERING BROAD AND DURABLE RESISTANCE TO GRAPEVINE FANLEAF VIRUS IN PLANTS

(75) Inventors: Marc Fuchs, Geneva, NY (US); Jonathan Oliver, Geneva, NY (US)

(73) Assignee: Cornell University, Ithaca, NY (US)

( * ) Notice: Subject to any disclaimer, the term of this patent is extended or adjusted under 35 U.S.C. 154(b) by 165 days.

(21) Appl. No.: 13/126,956

(22) PCT Filed: Nov. 2, 2009

(86) PCT No.: PCT/US2009/063013
§ 371 (c)(1),
(2), (4) Date: May 19, 2011

(87) PCT Pub. No.: WO2010/051548
PCT Pub. Date: May 6, 2010

(65) Prior Publication Data
US 2011/0296553 A1 Dec. 1, 2011

Related U.S. Application Data

(60) Provisional application No. 61/110,405, filed on Oct. 31, 2008.

(51) Int. Cl.
*C07H 21/04* (2006.01)
*C07H 21/02* (2006.01)
*C12N 15/79* (2006.01)

(52) U.S. Cl.
USPC .............. 800/285; 536/23.72; 435/320.1; 800/301; 800/298; 800/280

(58) Field of Classification Search
None
See application file for complete search history.

(56) References Cited

U.S. PATENT DOCUMENTS

| | | | |
|---|---|---|---|
| 5,583,021 | A | 12/1996 | Dougherty et al. |
| 6,369,296 | B1 | 4/2002 | Ratcliff et al. |
| 6,667,426 | B1 | 12/2003 | Gonsalves et al. |
| 6,841,720 | B1 * | 1/2005 | Draper et al. ............ 800/287 |
| 7,211,710 | B2 | 5/2007 | Gonsalves et al. |
| 2003/0226172 | A1 | 12/2003 | Gonsalves et al. |
| 2008/0016593 | A1 | 1/2008 | Gal-On et al. |

FOREIGN PATENT DOCUMENTS

| | | |
|---|---|---|
| EP | 0626998 B1 | 10/2001 |
| KR | 10-2007-0021156 A | 2/2007 |
| KR | 10-2007-0021156 A | 2/2007 |
| WO | WO 93-17098 A1 | 9/1993 |
| WO | WO-2005/079162 | 9/2005 |
| WO | WO 2005-079162 A2 | 9/2005 |

OTHER PUBLICATIONS

Andret-Link et al, 2004, Virology, 320:12-22.*
Jelly et al, 2012, Transgenic Res., 21:1319-1327.*
Barbier et al, 2000, Acta Hort., 528:385-388).*
Database EMBL, "Grapevine Fanleaf Virus RNA-Dependent RNA Polymerase-Like Gene, Partial Sequence," retrieved from EBI Accession No. EM_VI:EF528585 Database Accession No. EF28585, dated May 1, 2007 (1 page).
Gadani et al., "Genetic Engineering of Plants for Virus Resistance," *Arch. Virol.* 115:1-21 (1990).
Supplementary European Search Report issued in European Application No. 09824233, dated Jun. 4, 2012.
Ritzenthaler, C. et al. Complete nucleotide sequence and genetic organization of grapevine fanleaf nepovirus RNA1. Journal of General Virology 2991, vol. 72, pp. 2357-2365.
Serghini, M.A. et al. RNA2 of grapevine fanleaf virus: sequence analysis and coat protein cistron location. Journal of General Virology 1990, vol. 71, pp. 1433-1441.
PCT International Search Report for PCT/US2009/063013, Jun. 9, 2009 (4 pages).
PCT Written Opinion of ISR for PCT/US2009/063013, Jun. 9, 2009 (5 pages).
PCT International Preliminary Report on Patentability for PCT/US2009/063013, May 3, 2011 (6 pages).
Examiner's Report issued in Chilean Patent Application No. 972-11, formally served Mar. 8, 2013 (21 pages) (English Language Translation Provided).
Ritzenthaler et al., "Complete nucleotide sequence and genetic organization of grapevine fanleaf nepovirus RNA1," *J. Gen. Virol.* 72:2357-2365 (1991).
Serghini et al., "RNA2 of grapevine fanleaf virus: sequence analysis and coat protein cistron location," *J. Gen. Virol.* 71:1433-1441 (1990).
Database EMBL, "Grapevine Fanleaf Virus Isolate NW Segment RNA2 Polyprotein P2 Gene, Complete Cds," retrieved from EBI Accession No. EM_VI:AY017338 Database Accession No. AY017338, dated Jun. 8, 2001 (3 pages).
Database EMBL, "Grapevine Fanleaf Virus RNA-Dependent RNA Polymerase-Like Gene, Partial Sequence," retrieved from EBI Accession No. EM_VI:EF528585 Database Accession No. EF528585, dated May 1, 2007 (1 page).
Database EMBL,"Arabis Mosaic Virus Isolate Lv Segment RNA1, Complete Sequence," retrieved from EBI Accession No. EM_VI:EU617326 Database Accession No. EU617326, dated Jul. 21, 2008 (4 pages).

\* cited by examiner

*Primary Examiner* — Ashwin Mehta
*Assistant Examiner* — Jason Deveau Rosen
(74) *Attorney, Agent, or Firm* — Clark & Elbing LLP

(57) ABSTRACT

The present invention relates to nucleic acid molecules useful for conferring broad and durable resistance to grapevine fanleaf virus in plants. The invention also relates to methods of enhancing resistance to plant pathogens and plants or plant components (such as grape plants) expressing such nucleic acid molecules. In addition, the invention relates to products (e.g., foodstuffs including beverages such as wine or juice) derived from grape plants transformed with such nucleic acids.

35 Claims, 2 Drawing Sheets

ENGINEERING BROAD AND DURABLE RESISTANCE TO GRAPEVINE FANLEAF VIRUS IN PLANTS

CROSS-REFERENCE TO RELATED APPLICATIONS

This application is the U.S. National Stage filing under 35 U.S.C. §371 of International Application No. PCT/US2009/063013, filed Nov. 2, 2009, which claims benefit of U.S. Provisional Patent Application No. 61/110,405, filed Oct. 31, 2008.

BACKGROUND OF THE INVENTION

The invention relates to disease resistance in plants.

Grapevine fanleaf virus (GFLV) is a grape nepovirus, which is transmitted from plant to plant by the dagger nematode, *Xiphinema index*. GFLV is the agent responsible for grapevine fanleaf disease, which occurs worldwide. The disease is named for the fanleaf shaped appearance of GFLV-infected leaves. It is one of the most damaging and widespread diseases of grapevine. Symptoms of GFLV infection include abnormal shoot morphology and discolorations of the leaves, yielding a fan-like appearance (Agrios, Plant Pathology, 3$^{rd}$ Edition, Academic Press, 1988, pp. 687-688). In addition, fruit production of infected vines is low, with grapevines producing small bunches having abnormal fruit set and ripening. Ultimately, infected grapevines degenerate and die.

Long range spread of GFLV is believed to be by use of infected planting material. While the natural host range is thought to be restricted to grape, GFLV is also transmissible to a wide range of herbaceous species by sap-rubbing inoculation.

Current strategies for controlling grapevine fanleaf disease and other nepovirus-induced diseases in vineyards include nematode control (for example, soil fumigation and use of other pesticides), breeding rootstocks for resistance to nematode feeding, breeding grapevines for resistance to GFLV, and planting certified disease-free grapevines. Accordingly, there exists a need for agents and methods useful for controlling GFLV as well as other viral plant disease.

SUMMARY OF THE INVENTION

We have discovered that constructs derived from multiple conserved regions of grapevine fanleaf virus (GFLV) provide broad-spectrum and durable resistance to GFLV. Accordingly, the invention provides purified nucleic acid molecules, vectors, cells, plants and plant parts, products, and methods useful for protecting plants from diseases caused by plant viruses.

In one embodiment, the invention features a substantially purified nucleic acid molecule having a first nucleic acid fragment and a second nucleic acid fragment. These first and second nucleic acid fragments are each substantially identical to one of fragment 1 through fragment 8 (SEQ ID NOs:1-8) or a complement thereof, with the proviso that the nucleic acid molecule has less than 99% sequence identity to GFLV RNA1 (SEQ ID NO:27) and GFLV RNA2 (SEQ ID NO:28) or a nucleic acid fragment thereof. In other embodiments, the nucleic acid molecule further includes a third nucleic acid fragment that is substantially identical to one of fragment 1 through fragment 8 or a complement thereof. In still other embodiments, the nucleic acid molecule is concatenate 463, 582, 714, 678, 123, 375, 168, 245, 12367845, or 375168 (SEQ ID NOs:17-26, respectively). Each of these nucleic acid molecules has been engineered to confer resistance to a plant pathogen on a plant expressing the nucleic acid molecule.

In still another embodiment, the nucleic acid molecule is operably linked to a promoter (for example, a developmentally-regulated, organelle-specific, tissue-specific, constitutive, or cell-specific promoter). In yet other embodiments, the promoter is inducible by one or more external agents. Such nucleic acid molecules are DNA or RNA.

In another aspect, the invention features a vector including any of the aforementioned nucleic acid molecules. In one embodiment, the nucleic acid molecule of the vector is operably linked, in a sense orientation or an anti-sense orientation, to a promoter.

In another aspect, the invention features a cell including any of the aforementioned nucleic acid molecules or any of the aforementioned vectors. Exemplary cells include bacterial, insect, mammalian, or plant cells.

In still other aspects, the invention features a plant or plant component which includes the aforementioned nucleic acid molecules or vectors. Such plants include monocots or dicots. Exemplary plants useful in the invention include grape, raspberry, strawberry, cherry, hop, black currant, currant, elder, rhubarb, lettuce, tomato, cucumber, celery, daffodil, or forsythia. Embodiments of such plants are grape plants and grape plant components such as a grape fruit, a somatic embryo, a scion, or a rootstock.

In another aspect, the invention features a method of enhancing resistance to a plant pathogen in a plant, the method including: (a) providing a plant cell that expresses any of the nucleic acid molecules or combinations described herein or vectors described herein; and (b) regenerating a plant or plant component from the plant cell, wherein the nucleic acid molecules is expressed in the plant, and wherein the plant has enhanced resistance to a plant pathogen compared to a corresponding untransformed plant. In one embodiment, the method provides enhanced resistance to a virus such as GFLV or arabis mosaic virus (ArMV). In other embodiments, the methods provides enhanced resistance to GFLV or ArMV, in, e.g., grape, raspberry, strawberry, cherry, hop, black currant, currant, elder, rhubarb, lettuce, tomato, cucumber, celery, daffodil and forsythia. In another embodiment, the methods provide enhanced resistance to GFLV in grape plants.

In other embodiments, any of the aforementioned nucleic acid molecules or any of the aforementioned vectors include a transgene found in the transgenic grapevine. In still other embodiments, the nucleic acid molecule is expressed in a sense or antisense orientation. In yet other embodiments, such nucleic acid molecules or vectors are expressed as a sense nontranslatable sequence (i.e., not translated into a protein because the nucleic acid molecule or vector has, for example, having an out-of-reading frame initiation codon with the remainder of the mRNA being out of frame).

Accordingly, in still another aspect, the invention features a method for enhancing resistance to viral disease in a grape plant cell, the method including transforming the grape plant cell with any of the nucleic acid molecules or combinations described herein or vectors described herein, wherein expression of the nucleic acid in the grape plant cell increases resistance of the grape plant cell to viral disease. In one embodiment, the method further includes propagating a grape plant from the plant cell. Exemplary grape plant cells include fruit cells, scion cells, or rootstock cells. And again, the method is useful for enhancing resistance of a grape plant to grapevine fanleaf disease.

In yet another aspect, the invention features a grape plant or grape plant tissue which includes any of the aforementioned nucleic acid molecules or any of the aforementioned vectors, wherein expression of the nucleic acid or vector in the grape plant cell increases resistance of the grape plant cell to viral disease.

In another aspect, the invention features a product derived from a grape plant transformed with any of the aforementioned nucleic acid molecules or any of the aforementioned vectors. In some embodiments, the product is a foodstuff (e.g., a jellies, raisins, grape pulp, a beverage such as wine or juice, or a chemical such as resveratrol).

The methods described herein are useful for providing disease resistance or tolerance or both on a variety of grapevines (e.g., *Vitis* spp., *Vitis* spp. hybrids, and all members of the subgenera *Euvitis* and *Muscadinia*) to viral pathogens (e.g., GFLV), including scion and rootstock cultivars. Exemplary scion cultivars include, without limitation, those which are referred to as table or raisin grapes and those used in juice and wine production such as Cabernet Franc, Cabernet Sauvignon, Chardonnay (e.g., CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Rootstock cultivars that are useful in the invention include, without limitation, *Vitis rupestris* Constantia, *Vitis rupestris* St. George, *Vitis california*, *Vitis girdiana*, *Vitis rotundifolia*, *Vitis rotundifolia* Carlos, Richter 110 (*Vitis berlandieri×rupestris*; "110R"), 101-14 Millarder et de Grasset (*Vitis riparia×rupestris*; "101-14. Mgt"), Teleki 5C (*Vitis berlandieri×riparia*), Courderc 3309 (*Vitis riparia× rupestris*; "C3309"), Riparia Gloire de Montpellier (*Vitis riparia*), 5BB Teleki (selection Kober, *Vitis berlandieri×riparia*), SO$_4$ (*Vitis berlandieri×rupestris*), 41B Millardet (*Vitis vinifera×berlandieri*), Ramsey (*Vitis champinii*), K5140 (*Vitis champinii×Vitis riparia*), and 039-16 (*Vitis vinifera× Muscadinia*).

The invention also features fruit, scions, rootstocks, somatic or zygotic embryos, cells, or seeds that are produced from any of the transgenic plants or plant components described herein.

Preferably, the grapevine useful in the invention is a member of the genus *Vitis*; and the grapevine component is a fruit, a somatic embryo, a scion, a rootstock, or a mother block. In other embodiments, the fanleaf disease is grapevine fanleaf disease caused by a grape nepovirus. In yet other embodiments, the nepovirus is a GFLV or an ArMV.

In another aspect, the invention features a vineyard including three or more transgenic grapevines or grapevine components each of which express one or more of the nucleic acid molecules described herein, wherein the nucleic acid molecule increases resistance of the transgenic grapevines or grapevine components in the vineyard to grapevine fanleaf disease.

The invention also features scions, rootstocks, somatic or zygotic embryos, cells, or seeds that are produced from any of the transgenic grapevines or grapevine components described herein. The invention also includes a grape cell which has been transformed with a nucleic acid molecule which is positioned for expression by operably linking the transgene to a plant expression control region that provides resistance to a viral pathogen. Such grape cells are then used to generate rootstocks, scions, somatic embryos, or seeds using methods that are known in the art (e.g., those described herein).

By "nucleic acid molecule" is meant a molecule, e.g., RNA or DNA, having a sequence of two or more covalently bonded, naturally occurring or modified nucleotides. The nucleic acid molecule may be, e.g., single or double stranded, and may include modified or unmodified nucleotides, or mixtures or combinations thereof. Various salts, mixed salts, and free acid forms are also included.

By "nucleic acid fragment" is meant a contiguous segment of a nucleic acid molecule. The length of a nucleic acid segment can range from at least one base pair (e.g., at least 10, 20, 30, 40, 50, 60, 70, 80, 90, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 330, 350, 400, 450, 500, 700, 1000, 1500, or 2000 base pairs) up to the full length of the nucleic acid molecule. When a nucleic acid molecule is herein referred to as having more than one nucleic acid fragment, it is understood that these nucleic acid fragments occupy non-overlapping portions of the nucleic acid molecule.

By "sequence identity" is meant (in the context of comparing the sequence of a nucleic acid molecule or a nucleic acid fragment to a reference sequence) that the nucleic acid molecule or nucleic acid fragment has the same sequence as the reference sequence or has a specified percentage of nucleotides that are the same at the corresponding locations within the reference sequence when the full length sequence of the nucleic acid molecule or nucleic acid fragment is optimally aligned with the full length of the reference sequence. Within this context, the percentage of nucleotides that are the same between two sequences is computed with reference to the length of the longer sequence. Sequence identity can be computed between DNA and DNA, RNA and RNA, or DNA and RNA. When a sequence identity is computed between DNA and RNA, it is well-appreciated in the art that thymidine residues are equivalent to uracil residues for purposes of this calculation. Furthermore, it is well-appreciated in the art that if the percent sequence identity of the reverse complement sequence to the reference sequence is greater than that of the forward sequence, then the percent sequence identity is the former quantity. The Needleman-Wunsch algorithm, for example, may be used to determine sequence identity based on optimal global alignments. Computer programs for determining nucleic acid sequence identity are publicly available at, for example, the European Bioinformatics Institute (EMBL-EBI) website. For example, in the following global sequence alignment between GFLV fragment 1 and Concatenate 714,

```
Fragment1        1                                                         0

Concatenate714   1  GGATCCAGAAGAAATTGAGATTGGTTCTCGTTTCTTCGATTTCACTTCGA       50

Fragment1        1                                                         0

Concatenate714  51  ATACTTGTAGGGTATCTATGGGTGAAAATCCGTTTGCTGCAATGATTGCC      100

Fragment1        1                                              ggtaccaga    9
                                                                |||||||||
Concatenate714 101  TGCCATGGATTGCATAGTGGTGCGGCCGCTCTAGCGTCGACGGTACCAGA      150
```

```
Fragment1          10 tgaattgtgctttccatatcctgatcctaagcagcccgccatccttagcg    59
                      ||||||||||||||||||||||||||||||||||||||||||||||||||
Concatenate714    151 TGAATTGTGCTTTCCATATCCTGATCCTAAGCAGCCCGCCATCCTTAGCG   200

Fragment1          60 cagaggatgaacgccttaagggaacgatccatgaaggatacactccgtta   109
                      ||||||||||||||||||||||||||||||||||||||||||||||||||
Concatenate714    201 CAGAGGATGAACGCCTTAAGGGAACGATCCATGAAGGATACACTCCGTTA   250

Fragment1         110 agggatggcatgaagaagtttgctgagccaatgtatctgctagaggaaaa   159
                      ||||||||||||||||||||||||||||||||||||||||||||||||||
Concatenate714    251 AGGGATGGCATGAAGAAGTTTGCTGAGCCAATGTATCTGCTAGAGGAAAA   300

Fragment1         160 actactcgatgaagttgcaggtgacatggttcagacgtggtatga        204
                      |||||||||||||||||||||||||||||||||||||||||||||
Concatenate714    301 ACTACTCGATGAAGTTGCAGGTGACATGGTTCAGACGTGGTATGACTCGA   350

Fragment1         205                                                       204

Concatenate714    351 GACCGGACCCCAGCTCCCTACTTTAGGGCTGTTGGGGCTTTTGCACCAAC   400

Fragment1         205                                                       204

Concatenate714    401 CCGGTCCGAGTTTGTTCGGGCCATTGTGGAAAGGCTCACCCGGCTACGGG   450

Fragment1         205                                                       204

Concatenate714    451 AGGAGTCGAGAGCTGCGGCACTCTTTGCCGAATTGCCAGGATCC         494
``` these two sequences have 43% sequence identity because 204 base pairs are aligned of 494 base pairs (the length of the longer sequence).

By "substantially identical" is meant (in the context of comparing the sequence of a nucleic acid molecule or a nucleic acid fragment to a reference sequence) that the sequences have a sequence identity, as calculated using methods described above, of at least 85% (e.g., at least 85%, 87%, 90%, 92%, 95%, 96%, 97%, 98%, 99%, or 100%).

By "enhanced resistance to a plant pathogen" is meant a greater level of resistance to a pathogen (e.g., a virus such as a GFLV or an ArMV) in a transgenic plant (or plant component or cell, seed, or somatic embryo thereof) than the level of resistance relative to a control plant (e.g., a non-transgenic plant). In one embodiment, the level of resistance to a pathogen in a transgenic plant is at least 5 to 10% (and preferably 20%, 30%, or 40%) greater than the resistance of a control plant. In other embodiments, the level of resistance to the pathogen is 50% greater, 60% greater, and more preferably even 75% or 90% greater than a control plant; with up to 100% resistance as compared to a control plant being most preferred. The level of resistance is measured using conventional methods. For example, the level of resistance to fanleaf disease may be determined by comparing physical features and characteristics (for example, plant height and weight, or by comparing disease symptoms, for example, delayed lesion development, reduced lesion size, leaf wilting and curling, mottling and necrosis of leaves, deformity of canes, number of internodes, mosiac rings on leaves, and discoloration of cells) of transgenic grapevines. Infectivity of a grape nepovirus (e.g., a GFLV or an ArMV) can also be monitored using, for example, standard ELISA, or any method disclosed herein.

By "operably linked" is meant that a gene and a regulatory sequence(s) are connected in such a way to permit gene expression when the appropriate molecules (e.g., transcriptional activator proteins) are bound to the regulatory sequence(s).

By "plant cell" is meant any self-propagating cell bound by a semi-permeable membrane and containing a plastid. A plant cell, as used herein, is obtained from, without limitation, seeds, suspension cultures, embryos, meristematic regions, callus tissue, protoplasts, leaves, roots, shoots, somatic and zygotic embryos, as well as any part of a reproductive or vegetative tissue or organ.

By "plant component" is meant a part, segment, or organ obtained from an intact plant or plant cell. Exemplary plant components include, without limitation, somatic embryos, fruit, leaves, fruits, scions, and rootstocks.

As used herein, a nucleic acid molecule, be it a naturally occurring molecule or otherwise may be "substantially purified," if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

As is discussed above, the inventors described nucleic acid molecules useful for providing transgenic grapevines with resistance against grapevine fanleaf disease caused by the virus, grapevine fanleaf virus. Accordingly, because there are few alternatives for controlling grapevine fanleaf virus on grapes, the invention provides a number of important advances and advantages for viticulturists. The invention, for example, facilitates an effective and economical means for protection against grapevine fanleaf disease and other grape nepovirus-induced diseases. Such protection reduces or minimizes the need for traditional chemical practices (for example, soil fumigation) typically used by viticulturists for controlling the spread of a grape nepovirus and provides protection against these disease-causing pathogens. In addition, because grape plants expressing such grape nepovirus sequences are less vulnerable to grape nepovirus infection and fanleaf disease, the invention further provides for increased production efficiency, as well as for improvements in, quality, color, flavor, and yield of grapes. Furthermore, because the invention reduces the necessity for chemical protection against grapevine pathogens, it benefits the environment where the vineyards are planted. The invention can also be used to provide protection from other diseases caused by nepoviruses (e.g., Arabis mosaic virus) in, for example, raspberry, strawberry, cherry, hop, black currant, currant, elder, rhubarb, lettuce, tomato, cucumber, celery, daffodil and forsythia.

Other features and advantages of the invention will be apparent from the following description of the preferred embodiments thereof, and from the claims.

DETAILED DESCRIPTION

Figure 1:
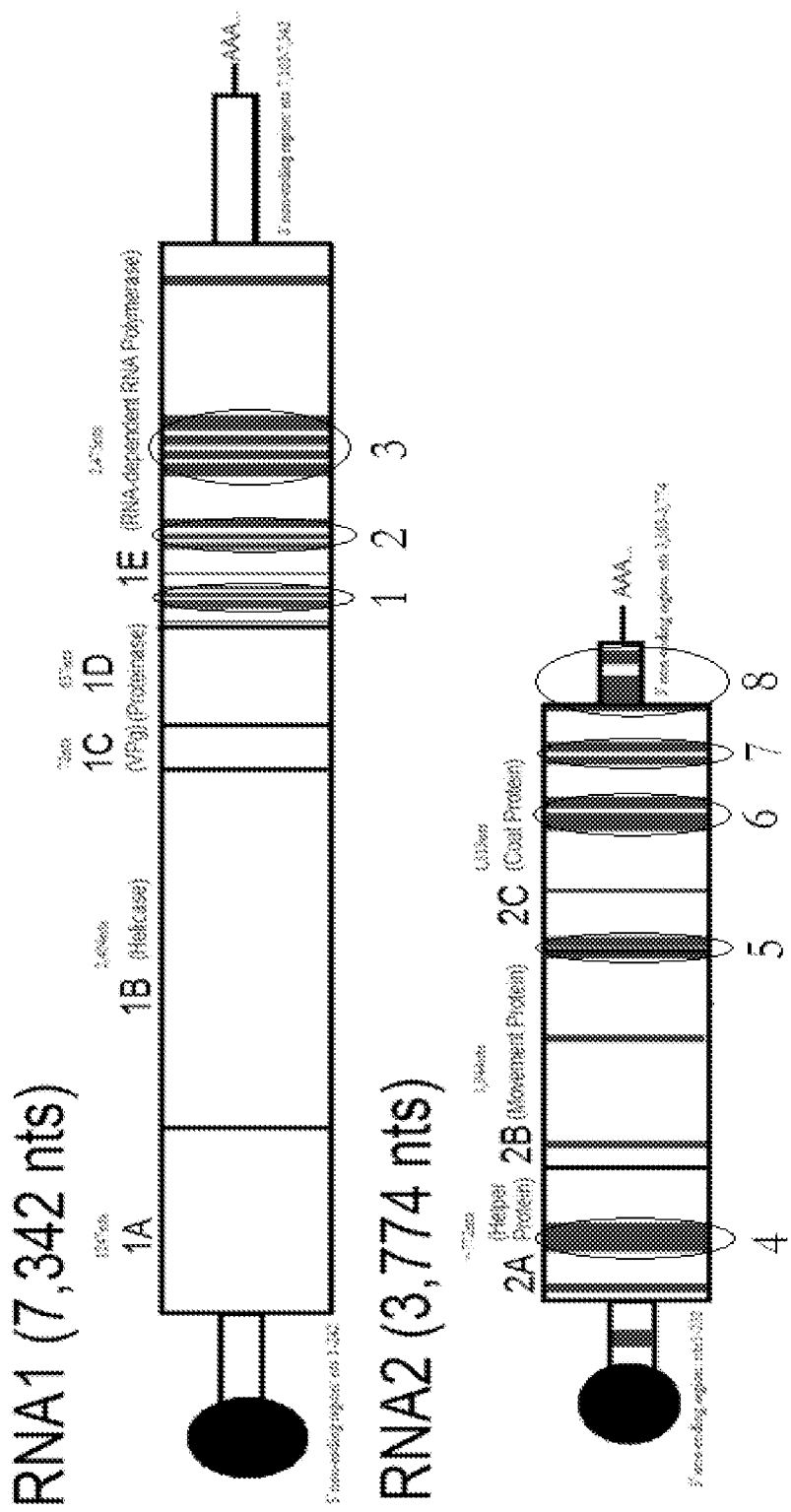
FIG. 1: Shows two genomic RNA's of GFLV. Regions of conservation identified by the GFLV sequence analysis are shown in black. Circles indicate groupings of these regions into the 8 chosen nucleic acid fragments. The drawing is not to scale.

Purified nucleic acid molecules, vectors, cells, plants, plant components, products, and methods of present invention relate to the protection of plants (e.g., grape plants) against plant diseases caused by plant viruses (e.g., GFLV and the serologically related ArMV). Additional details of the invention are provided below.

Nepovirus

Nepovirus is a genus of viruses in the family Comoviridae that are transmitted by nematodes. Nepoviruses are classified as type IV viruses under the Baltimore system; that is, they have a two part, single-stranded, RNA genome. These two segments of the RNA genome, RNA1 and RNA2, are separately encapsulated into icosahedral viral particles. RNA1, approximately 8,000 base pairs in length, encodes genes important for replication of the virus (e.g. RNA-dependent RNA Polymerase). RNA2, between 4000 to 7000 base pairs in length, has genes encoding Movement protein and Coat protein, and is important for cell-cell transmission of the virus. Each RNA has a 3' poly(A) tract. Included in the genus of nepovirus are arabis mosaic virus (ArMV) and grapevine fanleaf virus (GFLV).

Grapevine Fanleaf Virus

Grapevine fanleaf virus is a grapevine pathogen that can be spread over long distances in soil and between plants nematodes. One vector for the disease is the nematode *Xiphinema index*. The virus can also be transmitted by seed and grafting. Grapevine fanleaf disease is a widespread viral disease of grapevine, caused by GFLV, that occurs in all vine growing regions. *Vitis* spp. is a major natural host of grapevine fanleaf disease. Grapevine fanleaf disease is characterized by malformations of leaves and canes and by various types of foliage discolourations of the foliage (e.g., mottling, yellowing, ringspots, line patterns). Grape bunches are reduced in number and size, and fruits lose sweetness and acidity. Losses in crop due to grapevine fanleaf disease can be very high (up to 90%). Local spread of the virus is difficult to control. The virus persists in the roots of lifted vines, and can remain in nematode vectors for several months. Controlling vectors by soil fumigation is difficult and ineffective, and other approaches such as prolonged fallow, crop rotation, tillage, and weed control are similarly ineffective.

Arabis Mosaic Virus

Arabis mosaic virus, also known as raspberry yellow dwarf virus or rhubarb mosaic virus, is serologically related to GFLV. ArMV occurs in many species of monocot and dicot plants. It has been shown to cause yellow dwarf in raspberry, mosaic and yellow crinkle in strawberry, stunted mottle in cucumber, chlorotic stunt in lettuce, stunting and necrosis in celery, yellow net in forsythia, and mosaic in rhubarb. ArMV also occurs in many other plants including grape, cherry, black currant, currant, elder, tomato, daffodil, sugar beet, hop, horseradish, Narcissus, rose, *Sambucus nigra, Ligustrum vulgare*, and white clover. Vectors for ArMV include the free-living, soil-inhabiting nematodes, *Xiphinema diversicaudatum* and *Xiphinema coxi*.

Methodology

Analysis of GFLV Sequence Information

We have analyzed GFLV genome sequence information and identified conserved stretches of sequence which may be incorporated into transgene constructs to provide resistance to a wide range of GFLV variants. Our analysis resulted in the identification of regions of the genome possessing high levels of conservation at the nucleotide level. Our searches focused on the variation of individual nucleotides. Only regions of the genome at least 20 bp in length containing greater than 95% conservation of greater than 85% of the individual nucleotides were chosen. Conservation within the RNA2 genomic RNA was determined through alignment of all the available GFLV sequence information using the ClustalX algorithm and identification of nucleotide positions where the dominant nucleotide was present 95% of the time. Conservation of the RNA-dependent RNA polymerase (RdRp) gene on the RNA1 genomic RNA was determined by alignment of the available GFLV sequence information with the closely related nepovirus ArMV and identification of regions of conservation using the same methodology described above. Conserved regions identified using these methods, as illustrated in FIG. 1, were utilized for subsequent construct development.

Transgene Construct Design

Following the analysis of GFLV sequence where conserved stretches of nucleotides from GFLV were identified, these stretches were grouped into eight larger regions (as circled in FIG. 1). These eight regions are shown in Table 1.

TABLE 1

Eight regions of RNA1 and RNA2 identified by GFLV sequence analysis as well as their length, the genes from which each region is derived, and the shorter regions of conservation included within each region.

| Region (from 5' end of RNA) | Total Length | Genes Included | Conserved Regions Included |
|---|---|---|---|
| 4743-4935nts (RNA1) | 193nts | RdRp | 4743-4807nts (65nts), 4851-4875nts (25nts), and 4903-4935nts (33nts) |
| 5300-5483nts (RNA1) | 184nts | RdRp | 5300-5342nts (43nts), 5368-5393nts(26nts), and 5431-5483nts(53nts) |
| 5746-6073nts (RNA1) | 328nts | RdRp | 5746-5813nts (68nts), 5824-5855 (32nts), 5868-5920nts (43nts), and 6001-6073nts (73nts) |
| 582-700nts (RNA2) | 119nts | Helper Protein (2A) | 582-700nts (119nts) |
| 1991-2137nts (RNA2) | 147nts | Movement (2B) and Coat Protein (2C) | 1991-2021nts (31nts) and 2088-2137nts (50nts) |
| 2811-2935nts (RNA2) | 125nts | CP (2C) | 2811-2874nts (64nts) and 2904-2935nts (32nts) |
| 3132-3232nts (RNA2) | 101nts | CP (2C) | 3132-3174nts (33nts) and 3207-3232nts (26nts) |
| 3531-3757nts (RNA2) | 227nts | CP (2C) and 3' Non-coding Region | 3531-3588nts (58nts) and 3692-3757nts (67nts) |

Following identification of these regions, eight nucleic acid fragments encompassing these regions were cloned from GFLV cDNA. The sequences of these eight nucleic acid fragments are given below:

Fragment 1

(SEQ ID NO: 1)
GGTACCAGAT GAATTGTGCT TTCCATATCC TGATCCTAAG CAGCCCGCCA TCCTTAGCGC

AGAGGATGAA CGCCTTAAGG GAACGATCCA TGAAGGATAC ACTCCGTTAA GGGATGGCAT

GAAGAAGTTT GCTGAGCCAA TGTATCTGCT AGAGGAAAAA CTACTCGATG AAGTTGCAGG

TGACATGGTT CAGACGTGGT ATGA

Fragment 2

(SEQ ID NO: 2)
CTTGTTGAGA GTAAAATTTT TGTCTTTTTC CCGCCTACTG ATGAAGAAGA GAGGCCACCT

GCCTTGTCAA GTGGGCATCA ATCCTTATAG TCGCGAATGG ACCGATTTGT ATCACCGCTT

AGGTGAACTC TCTGATGTCG GATACAATTG TGATTATAAG GCTTTTGATG GCCTAATTAC

GGAGCAAATT TTGAGT

Fragment 3

(SEQ ID NO: 3)
TACCTATGGT GATGATAATG TCTTCACTGT GGCACAATCT GTCATGCAGT ATTTTACTGG

CGATGCTCTG AAAATGCAAA TGGCAAAGCT TGGGGTAACT ATTACTGATG GGAAAGATAA

GTCTCTTTCC ACTATTCCAG CCCGTCCACT GCTGGAATTA GAGTTTTTGA AACGTGGATT

TGTTAGAAGC TCTGGGGGTA TGATAAATGC GCCTTTGGAA AAATTATCAA TAATGAGTTC

TTTGGTCTAC ATCAGAAGTG ATGGCTCAGA CATGTTGCAG AAACTATTGG ACAATGTTAA

TACTGCACTT GTCGAGCTTT ATCTACATGG TGA

Fragment 4

(SEQ ID NO: 4)
CCCCAGCTCC CTACTTTAGG GCTGTTGGGG CTTTTGCACC AACCCGGTCC GAGTTTGTTC

GGGCCATTGT GGAAAGGCTC ACCCGGCTAC GGGAGGAGTC GAGAGCTGCG GCACTCTTTG

CCGAATTGCC A

Fragment 5

(SEQ ID NO: 5)
TGATAGAAAC GTTGATCTTC CTCAACTTGA GGCTGAGCCC AGACTGAGCT CAACCGTGAG

AGGGCTAGCC GGCAGAGGAG TAATCTACAT TCCCAAGGAT TGCCAGGCAA ATAGATACTT

GGGCACCCTG AATATACGTG ATATGATCTC AGACTTCAAG

Fragment 6

(SEQ ID NO: 6)
TTAGTGAGTG GAACGGGACC ACTATGGACT GGAATGAACT TTTTAAGTAT CCCGGGGTGT

ATGTGGAAGA GGACGGAAGT TTTGAAGTAA AGATTCGCTC TCCATATCAC CGAACTCCTG

CCAGATTGCT TGCTGGTCAA AGTCAG

Fragment 7

(SEQ ID NO: 7)
AGAAGAAATT GAGATTGGTT CTCGTTTCTT CGATTTCACT TCGAATACTT GTAGGGTATC

TATGGGTGAA AATCCGTTTG CTGCAATGAT TGCCTGCCAT GGATTGCATA GTGGT

Fragment 8

(SEQ ID NO: 8)
TTTAGCTTTT ATGGTAGAAC CAGTTTCCCA GTCTAGTGAT ACGTAGATAT CTAGGGTATC

TGACTTTAAA AGACCCAAGT GTATATATGT GTTTTGTCAG TAGCATGTAT TATTTTGTGT

TATAATTTGT TTTAACTTGT TTTCCGCTTT TGTGTGTTTA GTTCATGCT TTTAGTGGCG

ACAGTGTGTT GTTTGTCCTT TGGACACACT TGCCTAGTTG CACGCAAAAA GATTTTTCCT

TTCTTTTTAC TG

Polymerase chain reaction (PCR) was used to amplify these nucleic acid fragments from F13 GFLV cDNA. Amplified nucleic acid fragments were subsequently ligated into various concatenates, with the aim of combining conserved regions from multiple genes (including the RNA-dependent RNA polymerase, helper protein, movement protein, and coat protein) within the GFLV genome to provide resistance against diverse GFLV variants (that is, to enable broad-spectrum resistance), rendering it more difficult for an individual GFLV strain to mutate to overcome the resistance provided by transgenes derived from these nucleic acid fragments.

The GFLV nucleic acid fragments may be concatenated in various ways. In one working example, two nucleic acid fragments substantially identical to fragments 1-8 (e.g., fragment 1+fragment 2, fragment 5+fragment 8, or fragment 4+fragment 7) are concatenated without any intervening sequences between the nucleic acid fragments. Alternatively, the two nucleic acid fragments are concatenated with one or more base pairs (e.g., 5, 10, 20, 50, 100, 200, 500, or 1000 base pairs) of intervening sequences between the nucleic acid fragments. The length and composition of intervening sequence between any two nucleic acid fragments of these concatenates may vary according to nucleic acid ligation techniques known in the art. The present concatenates may also have flanking sequences of one or more base pairs (e.g., 5, 10, 20, 50, 100, 200, 500, or 1000 base pairs) on one or both sides of the nucleic acid fragments. The nucleic acid fragments may each be oriented, independently, in a sense or anti-sense orientation (e.g., sense/sense, sense/anti-sense, anti-sense/sense, or anti-sense/anti-sense).

In another working example, three nucleic acid fragments substantially identical to fragments 1-8 are concatenated without any intervening sequences between these nucleic acid fragments. Alternatively, the three nucleic acid fragments may have one or more base pairs (e.g., 5, 10, 20, 50, 100, 200, 500, or 1000 base pairs) of intervening sequence between any two consecutive nucleic acid fragments. These concatenates may also have one or more base pairs (e.g., 5, 10, 20, 50, 100, 200, 500, or 1000 base pairs) of sequence flanking one or both sides of the nucleic acid fragments. Each nucleic acid fragment in the concatenation may have a percent sequence identity to fragments 1-8 SEQ ID NOs:1-8 that varies independently from those of other nucleic acid fragments in the concatenate.

Exemplary nucleic acid molecules having three nucleic acid fragments substantially identical to fragments 1-8 are described in the following concatenates. As used herein, the name of each concatenate is a set of digits corresponding, in order, to the nucleic acid fragments present in the concatenate. For example, concatenate 463 includes fragment 4, fragment 6, and fragment 3, in that order.

```
Concatenate 463
                                                 (SEQ ID NO: 17)
GGATCCCCCCAGCTCCCTACTTTAGGGCTGTTGGGGCTTTTGCACCAACCCGGTCCGAGTT

TGTTCGGGCCATTGTGGAAAGGCTCACCCGGCTACGGGAGGAGTCGAGAGCTGCGGCACT

CTTTGCCGAATTGCCAGGGCCCTTAGTGAGTGGAACGGGACCACTATGGACTGGAATGAA

CTTTTTAAGTATCCCGGGGTGTATGTGGAAGAGGACGGAAGTTTTGAAGTAAAGATTCGCT

CTCCATATCACCGAACTCCTGCCAGATTGCTTGCTGGTCAAAGTCAGGCGGCCGCTCTAGC

GTCGACTACCTATGGTGATGATAATGTCTTCACTGTGGCACAATCTGTCATGCAGTATTTT

ACTGGCGATGCTCTGAAAATGCAAATGGCAAAGCTTGGGGTAACTATTACTGATGGGAAA

GATAAGTCTCTTTCCACTATTCCAGCCCGTCCACTGCTGGAATTAGAGTTTTTGAAACGTG

GATTTGTTATAAGCTCTGGGGGTATGATAAATGCGCCTTTGGAAAAATTATCAATAATGAG

TTCTTTGGTCTACATCAGAAGTGATGGCTCAGACCTGTTGCAGAAACTATTGGACAGTGTT

AATACTGCACTTGTCCAGCTTTTCTAGCTGGTGAGGATCC

Concatenate 582
                                                 (SEQ ID NO: 18)
GGATCCTGATAGAAACGTTGATCTTCCTCAACTTGAGGCTGAGCCCAGACTGAGCTCAACC

GTGAGAGGGCTAGCCGGCAGAGGAGTAATCTACATTCCCAAGGATTGCCAGGCAAATAGA

TACTTGGGCACCCTGAATATACGTGATATGATCTCAGACTTCAAGGGGCCCTTTAGCTTTT

ATGGTAGAACCAGTTTCCCAGTCTAGTGATACGTAGATATCTAGGGTATCTGACTTTAAAA

GACCCAAGTGTATATATGTGTTTTGTCAGTAGCATGTATTATTTTGTGTTATAATTTGTTTT

AACTTGTTTTCCGCTTTTGTGTGTTTAGTTTCATGCTTTTAGTGGCGACAGTGTGTTGTTTG

TCCTTTGGACACACTTGCCTAGTTGGACGCAAAAAGATTTTTCCTTTCTTTTTACTGGCGGC

CGCTCTAGCGTCGACCTTGTTGAGAGTAAAATTTTTGTCTTTTTCCCGCCTACTGATGAAGA

AGAGAGGCCACCTGCCTTGTCAAGTGGGCATCAATCCTTATAGTCGCGAATGGACCGATTT

GTATCACCGCTTAGGTGAACTCTCTGATGTCGGATACAATTGTGATTATAAGGCTTTTGAT

GGCCTAATTACGGAGCAAATTTTGAGTGGATCC

Concatenate 714
                                                 (SEQ ID NO: 19)
GGATCCAGAAGAAATTGAGATTGGTTCTCGTTTCTTCGATTTCACTTCGAATACTTGTAGG

GTATCTATGGGTGAAAATCCGTTTGCTGCAATGATTGCCTGCCATGGATTGCATAGTGGTG
```

-continued

CGGCCGCTCTAGCGTCGACGGTACCAGATGAATTGTGCTTTCCATATCCTGATCCTAAGCA

GCCCGCCATCCTTAGCGCAGAGGATGAACGCCTTAAGGGAACGATCCATGAAGGATACAC

TCCGTTAAGGGATGGCATGAAGAAGTTTGCTGAGCCAATGTATCTGCTAGAGGAAAAACT

ACTCGATGAAGTTGCAGGTGACATGGTTCAGACGTGGTATGACTCGAGACCGGACCCCAG

CTCCCTACTTTAGGGCTGTTGGGGCTTTTGCACCAACCCGGTCCGAGTTTGTTCGGGCAT

TGTGGAAAGGCTCACCCGGCTACGGGAGGAGTCGAGAGCTGCGGCACTCTTTGCCGAATT

GCCAGGATCC

Concatenate 678
(SEQ ID NO: 20)
GGATCCTTAGTGAGTGGAACGGGACCACTATGGACTGGAATGAACTTTTTAAGTATCCCGG

GGTGTATGTGGAAGAGGACGGAAGTTTTGAAGTAAAGATTCGCTCTCCATATCACCGAAC

TCCTGCCAGATTGCTTGCTGGTCAAAGTCAGGCGGCCCAGAAGAAATTGAGATTGGTTCTC

GTTTCTTCGATTTCACTTCGAATACTTGTAGGGTATCTATGGGTGAAAATCCGTTTGCTGCA

ATGATTGCCTGCCATGGATTGCATAGTGGTGCGGCCCTTTAGCTTTTATGGTAGAACCAGT

TTCCCAGTCTAGTGATACGTAGATATCTAGGGTATCTGACTTTAAAAGACCCAAGTGTATA

TATGTGTTTTGTCAGTAGCATGTATTATTTTGTGTTATAATTTGTTTTAACTTGTTTTCCGCT

TTTGTGTGTTTAGTTTCATGCTTTTAGTGGCGACAGTGTGTTGTTTGTCCTTTGGACACACT

TGCCTAGTTGGACGCAAAAAGATTTTTCCTTTCTTTTTACTGGGATCC

Concatenate 123
(SEQ ID NO: 21)
GGATCCGGTACCAGATGAATTGTGCTTTCCATATCCTGATCCTAAGCAGCCCGCCATCCTT

AGCGCAGAGGATGAACGCCTTAAGGGAACGATCCATGAAGGATACACTCCGTTAAGGGAT

GGCATGAAGAAGTTTGCTGAGCCAATGTATCTGCTAGAGGAAAAACTACTCGATGAAGTT

GCAGGTGACATGGTTCAGACGTGGTATGACTCGACCTTGTTGAGAGTAAAATTTTTGTCTT

TTTCCCGCCTACTGATGAAGAAGAGAGGCCACCTGCCTTGTCAAGTGGGCATCAATCCTTA

TAGTCGCGAATGGACCGATTTGTATCACCGCTTAGGTGAACTCTCTGATGTCGGATACAAT

TGTGATTATAAGGCTTTTGATGGCCTAATTACGGAGCAAATTTTGAGTCTCGACTACCTAT

GGTGATGATAATGTCTTCACTGTGGCACAATCTGTCATGCAGTATTTTACTGGCGATGCTC

TGAAAATGCAAATGGCAAAGCTTGGGGTAACTATTACTGATGGGAAAGATAAGTCTCTTT

CCACTATTCCAGCCCGTCCACTGCTGGAATTAGAGTTTTTGAAACGTGGATTTGTTAGAAG

CTCTGGGGGTATGATAAATGCGCCTTTGGAAAAATTATCAATAATGAGTTCTTTGGTCTAC

ATCAGAAGTGATGGCTCAGACATGTTGCAGAAACTATTGGACAATGTTAATACTGCACTTG

TCGAGCTTTATCTACATGGTGAGGATCC

Concatenate 375
(SEQ ID NO: 22)
GGATCCTACCTATGGTGATGATAATGTCTTCACTGTGGCACAATCTGTCATGCAGTATTTT

ACTGGCGATGCTCTGAAAATGCAAATGGCAAAGCTTGGGGTAACTATTACTGATGGGAAA

GATAAGTCTCTTTCCACTATTCCAGCCCGTCCACTGCTGGAATTAGAGTTTTTGAAACGTG

GATTTGTTAGAAGCTCTGGGGGTATGATAAATGCGCCTTTGGAAAAATTATCAATAATGAG

TTCTTTGGTCTACATCAGAAGTGATGGCTCAGACATGTTGCAGAAACTATTGGACAATGTT

AATACTGCACTTGTCGAGCTTTATCTACATGGTGACTCGAGACCGGCGGGCCCAGAATAAA

TTGAGATTGGTTCTCGTTTCTTCGATTTCACTTCGAATACTTGTAGGGTATCTATGGGTGAA

AATCCGTTTGCTGCAATGATTGCCTGCCATGGATTGCATAGTGGTGCGGCCGCTCCGGATG

-continued
```
ATAGAAATCGTTGATCTTCCTCAACTTGAGGCTGAGCCCAGACTGACCTCAACCGTGAGAG

GGCTAGCCGGCAAAGGAGTAATCTACTTTCCCAAGGATTGCCAGGCAAATAGATACTTGG

CCACCCTGAATATACGTGATATGATCTCAGACTTCAAGGGATCC

Concatenate 168
                                                    (SEQ ID NO: 23)
GGATCCGGTACCAGATGAATTGTGCTTTCCATATCCTGATCCTAAGCAGCCCGCCATCCTT

AGCGCAGAGGATGAACGCCTTAAGGGAACGATCCATGAAGGATACACTCCGTTAAGGGAT

GGCATGAAGAAGTTTGCTGAGCCAATGTATCTGCTAGAGGAAAAACTACTCGATGAAGTT

GCAGGTGACATGGTTCAGACGTGGTATGACTCGAGACCGGCGGGCCCTTAGTGAGTGGAA

CGGGACCACTATGGACTGGAATGAACTTTTTAAGTATCCCGGGGTGTATGTGGAAGAGGA

CGGAAGTTTTGAAGTAAAGATTCGCTCTCCATATCACCGAACTCCTGCCAGATTGCTTGCT

GGTCAAAGTCAGGCGGCCCTTTAGCTTTTATGGTAGAACCAGTTTCCCAGTCTAGTGATAC

GTAGATATCTAGGGTATCTGACTTTAAAAGACCCAAGTGTATATATGTGTTTTGTCAGTAG

CATGTATTATTTTGTGTTATAATTTGTTTTAACTTGTTTTCCGCTTTTGTGTGTTTAGTTTCA

TGCTTTTAGTGGCGACAGTGTGTTGTTTGTCCTTTGGACACACTTGCCTAGTTGGACGCAA

AAAGATTTTTCCTTTCTTTTTACTGGGATCC

Concatenate 245
                                                    (SEQ ID NO: 24)
GGATCCCTTGTTGAGAGTAAAATTTTTGTCTTTTTCCCGCCTACTGATGAAGAAGAGAGGC

CACCTGCCTTGTCAAGTGGGCATCAATCCTTATAGTCGCGAATGGACCGATTTGTATCACC

GCTTAGGTGAACTCTCTGATGTCGGATACAATTGTGATTATAAGGCTTTTGATGGCCTAAT

TACGGAGCAAATTTTGAGTCTCGAGACCGGAGCGGCCCTGGCAATTTGGCAAAGAGTGCC

GCAGCTCTCGACTCCTCCCGTAGCCGGGTGAGCCTTTCCACAATGGCCCGAACAAACTCGG

ACCGGGTTGGTGCAAAAGCCCCAACAGCCCTAAAGTAGGGAGCTGGGGTCCGGATGATAG

AAACGTTGATCTTCCTCAACATGAGGCTGAGCCCAGACTGTGCTCAACCGTGAGAGGGCTA

GCCGGCAGAGGAGTAATCTACATTCCCAAGGATTGCCAGGCAAATAGATACTTGGGCACC

CTGAATATACGTGATATGATCTCAGACTTCAAGGGATCC
```

Other working examples feature nucleic acid molecules having more than 3 nucleic acid fragments substantially identical to fragments 1-8. For example, a nucleic acid molecule of the present invention may have 4 nucleic acid fragments substantially identical to fragments 1-8 (e.g., fragment 2+fragment 4+fragment 5+fragment 7 or fragment 3+fragment 1+fragment 6+fragment 1). In another example, a nucleic acid molecule of the present invention may have 5 nucleic acid fragments substantially identical to fragments 1-8 (e.g., fragment 2+fragment 4+fragment 5+fragment 7+fragment 2). In another example, a nucleic acid molecule of the present invention may have 6 nucleic acid fragments substantially identical to fragments 1-8 (e.g., fragment 3+fragment 7+fragment 5+fragment 1+fragment 6+fragment 8, as described below in concatenate 375168).

```
Concatenate 375168
                                                    (SEQ ID NO: 25)
GGATCCCAGTAAAAAGAAAGGAAAAATCTTTTTGCGTCCAACTAGGCAAGTGTGTCCAAA

GGACAAACAACACACTGTCGCCACTAAAAGCATGAAACTAAACACACAAAAGCGGAAAAC

AAGTTAAAACAAATTATAACACAAAATAATACCTGCTACTGACAAAACACATATATACACT

TGGGTCTTTTAAGTCAGATACCCTAGATATCTACGTATCACTAGACTGGGAAACTGGTTCT

ACCATAAAAGCTAAAGGGCCGCCTGACTTTGACCAGCAAGCAATCTGGCAGGAGTTCGGT

GATATGGAGAGCGAATCTTTACTTCAAAACTTCCGTCCTCTTCCACATACACCCCGGGATA

CTTAAAAAGTTCATTCCAGTCCATAGTGGTCCCGTTCCACTCACTAAGGGCCCGCCGGTCT

CGAGTCATACCACGTCTGAACCATGTCACCTGCAACTTCATCGAGTAGTTTTTCCTCTAGC
```

```
-continued
AGATACATTGGCTCAGCAAACTTCTTCATGCCATCCCTTAACGGAGTGTATCCTTCATGGA

TCGTTCCCTTAAGGCGTTCATCCTCTGCGCTAAGGATGGCGGGCTGCTTAGGATCCCTTGA

AGTCTGAGATCATATCACGTATATTCAGGGTGCCCAAGTATCTATTTGCCTGGCAATCCTT

GGGAATGTAGATTACTCCTCTGCCGGCTAGCCCTCTCACGGTTGAGCTCAGTCTGGGCTCA

GTCTCAAGTTGAGGAAGATCAACGTTTCTATCATCCGGAGCGGCCGCACCACTATGCAATC

CATGGCAGGCAATCATTGCAGCAAACGGATTTTCACCCATAGATACCCTACAAGTATTCGA

AGTGAAATCGAAGAAACGAGAACCAATCTCAATTTCTTCTGGGCCCGCCGGTCTCGAGTCA

CCATGTAGATAAAGCTCGACAAGTGCAGTATTAACATTGTCCAATAGTTTCTGCAACATGT

CTGAGCCATCACTTCTGATGTAGACCAAAGAATTCATTATTGATAATTTTTCCAAAGGCGC

ATTTATCATACCCCCAGAGCTTCTAACAAATCCACGTTTCAAAAACTCTAATTCCAGCAGT

GGACGGGCTGGAATAGTGGAAAGGGACTTATCTCTCCCATCAGTAATAGTTACCCCAAGCT

TTGCCATTTGCATTTTCAGAGCATCGCCAGTAAAATACTGCAGACAGATTGTGCCACAGTG

AAGACATTATCATCACCATAGGTAGGATCC
```

Yet other working examples feature nucleic acid molecules having more than 6 (e.g., 7, 8, or more) nucleic acid fragments substantially identical to fragments 1-8. A concatenate having 8 nucleic acid fragments, concatenate 12367845, is described below:

```
Concatenate 12367845
                                                    (SEQ ID NO: 26)
GGATCCGGTACCCGATGAATTGTGCTTTCCATATCCTGATCCTAAGCAGCCCGCCATCCTT

AGCGCAGAGGATGAACGCCTTAAGGGAACGATCCATGAAGGATACACTCCGTTAAGGGAT

GGCATGAAGAAGTTTGCTGAGCCAATGTATCTGCTAGAGGAAAAACTACTCGATGAAGTT

GCAGGTGACATGGTTCAGACGTGGTATGACTCGACCTTGTTGAGAGTAAAATTTTTGTCTT

TTTCCCGCCTACTGATGAAGAAGAGAGGCCACCTGCCTTGTCAAGTGGGCATCAATCCTTA

TAGTCGCGAATGGACCGATTTGTATCACCGCTTAGGTGAACTCCCTGATGTCGGATACAAT

TGTGATTATAAGGCTTTTGATGGCCTAATTACGGAGCAAATTTTGAGTCTCGACTACCTAT

GGTGATGATAATGTCTTCACTGTGGCACAATCTGTCATGCAGTACTTTACTGGCGATGCTC

TGAAAATGCAAATGGCAAAGCTTGGGGTAACTATTACTGATGGGAAAGATAAGTCTCTTT

CCACTATTCCAGCCCGTCCACTGCTGGAATTAGAGTTTTTGAAACGTGGATTTGTTAGAAG

CTCTGGGGGTATGATAAATGCGCCTTTGGAAAAATTATCAATAATGAGTTCTTTGGTCTAC

ATCAGAAGTGATGGCTCAGACATGTTGCAGAAACTATTGGACAATGTTAATACTGCACTTG

TCGAGCTTTATCTACATGGTGACTCGGGACCGGCGGCCCTTAGTGAGTGGAACGGGACC

ACTATGGACTGGAATGAACTTTTTAAGTATCCCGGGGTGTATGTGGAAGAGGACGGAAGT

TTTGAAGTAAAGATTCGCTCTCCATATCACCGAACTCCTGCCAGATTGCTTGCTGGTCAAA

GTCAGGCGGCCCAGAAGAAATTGAGATTGGTTCTCGTTTCTTCGATTTCACTTCGAATACT

TGTAGGGTATCTATGGGTGAAAATCCGTTTGCTGCAATGATTGCCTGCCATGGATTGCATA

GTGGTGCGGCCCTTTAGCTTTTATGGTAGAACCAGTTTCCCAGTCTAGTGATACGTAGATA

TCTAGGGTATCTGGCTTTAAAAGACCCAAGTGTATATATGTGTTTTGTCAGTAGCATGTAT

TATCTTGTGTTATAATTTGTTTTAACTTGTTTTCCGCTTTTGTGTGTTTAGTTTCATGCTTTT

AGTGGCGACAGTGTGTTGTTTGTCCTTTGGACACACTTGCCTAGTTGGACGCAAAAAGATT

TTTCCTTTCTTTTTACTGGCGGCCGCTCCGGACCCCAGCTCCCTACTTTAGGGCTGTTGGGG
```

```
                                -continued
CTTTTGCACCAACCCGGTCCGAGTTTGTTCGGGCCATTGTGGAAAGGCTCACCCGGCTACG

GGAGGAGTCGAGAGCTGCGGCACTCTTTGCCGAATTGCCAGGGCCGCTCCGGATGATAGA

AACGTTGATCTTCCTCAACTTGAGGCTGAGCCCAGACTGAGCTCAACCGTGAGAGGGCTAG

CCGGCAGAGGAGTAATCTACATTCCCAAGGATTGCCAGGCAAATAGATACTTGGGCGCCC

TGAATATACGTGATATGATCTCAGACTTCAAGGGATCC
```

In another working example, the nucleic acid molecule includes a nucleic acid fragment that is substantially identical to concatenate 463, 582, 714, 678, 123, 375, 168, 245, 12367845, or 375168 (SEQ ID NOs:17-26).

Any of the nucleic acid molecules described herein may contain more than one copy of the same nucleic acid fragment (e.g., fragment 6+fragment 7+fragment 7 (i.e., a 677 concatenate)). In some embodiments, all of the nucleic acid fragments in the molecule are the same nucleic acid fragment (e.g., fragment 1+fragment 1 (i.e., a 11 concatenate) or fragment 2+fragment 2+fragment 2 (i.e., a 222 concatenate)).

Other exemplary nucleic acid molecules include, for example, SEQ ID NOs:9-16.

Construction of Plant Transgenes

Any of the aforementioned nucleic acid molecules may be expressed as a sense translatable or sense nontranslatable mRNA transcript or as an antisense mRNA transcript by a stably-transfected grape cell line or by a transgenic grapevine or grapevine component. A number of vectors suitable for either stable or extrachromosomal transfection of plant cells, or for the establishment of transgenic plants are available to the public. Methods for constructing such cell lines are also well known in the art.

Typically, plant expression vectors include (1) a cloned gene (for example, a nucleic acid molecule which expresses a sense translatable, sense nontranslatable, or anti-sense grape nepovirus RNA) under the transcriptional control of 5' and 3' expression control sequences and (2) a dominant selectable marker. Such plant expression vectors may also contain, if desired, a promoter regulatory region (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Once the desired nucleic acid molecule is obtained as described above, it may be manipulated in a variety of ways known in the art. For example, a nucleic acid molecule may, if desired, be combined with other nucleic acid molecules in a variety of ways. In its component parts, a nucleic acid molecule is combined in a construct having a transcription initiation control region capable of promoting transcription in a host grapevine cell.

In general, the constructs involve regulatory regions functional in plants. For example, the sense translatable sequence for a nucleic acid molecule may be joined at its 5' end to transcription initiation regulatory region, e.g., a sequence naturally found in the 5' upstream region of a plant structural gene. In another example, the sense nontranslatable sequence for a nucleic acid molecule may be joined at its 5' end to a transcription initiation regulatory region. In yet another example, the antisense sequence for a nucleic acid molecule may be joined at its 5' end to a transcription initiation regulatory region. Numerous transcription initiation regions are available which provide for constitutive or inducible regulation.

For applications where developmental, cell, tissue, hormonal, or environmental expression is desired, appropriate 5' upstream non-coding regions are obtained from other genes, for example, from genes regulated during meristem development, seed development, embryo development, leaf development, stem development, or tendril development.

Regulatory transcript termination regions may also be provided in DNA constructs of this invention as well. Transcript termination regions may be provided by the nucleic acid molecule or any convenient transcription termination region derived from a different gene source (for example, the NOS or 35S CaMV terminators). The transcript termination region will contain preferably at least 1 to 3 kb of sequence 3' to the structural gene from which the termination region is derived. Plant expression constructs having the nucleic acid molecule of the present invention as the sequence of interest for expression (in either the antisense orientation or sense translatable or sense nontranslatable production of mRNA) may be employed with a wide variety of grapevines. Such genetically-engineered plants are useful for a variety of industrial and agricultural applications. Importantly, this invention is applicable to all grapevines or grapevine components, and will be readily applicable to any new or improved transformation or regeneration methods of grape.

The expression constructs include at least one promoter operably linked to at least one sense translatable, sense nontranslatable, or antisense sequence (combinations are also desirable). An example of a useful plant promoter according to the invention is a caulimovirus promoter, for example, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter. The CaMV promoter is also highly active in monocots. Moreover, activity of this promoter can be further increased (i.e., between 2 to 10 fold) by duplication of the CaMV 35S promoter.

Other useful plant promoters include, without limitation, the nopaline synthase (NOS) promoter, the octopine synthase promoter, the rice actin promoter, the cyclase promoter, and the cassava vein mosaic virus promoter. Still other exemplary promoters useful in the invention include, without limitation, commelina yellow mottle virus promoter, sugar cane badna virus promoter, rice tungro bacilliform virus promoter, maize streak virus element, and wheat dwarf virus promoter.

For certain applications, it may be desirable to express any of the nucleic acid molecules in an appropriate tissue, at an appropriate level, or at an appropriate developmental time. For this purpose, there are an assortment of gene promoters, each with its own distinct characteristics embodied in its regulatory sequences, shown to be regulated in response to inducible signals such as the environment, hormones, and/or developmental cues. These include, without limitation, gene promoters that are responsible for heat-regulated gene expression, light-regulated gene expression; the maize rbcS promoter; the chlorophyll a/b-binding protein gene; the Arabssu promoter; or the rice rbs promoter, hormone-regulated gene expression (for example, the abscisic acid (ABA) responsive sequences from the $E_m$ gene of wheat; the ABA-inducible HVA1 and HVA22, and rd29A promoters described for barley and *Arabidopsis*); and wound-induced gene expression (for example, of wunI), organ-specific gene expression (for example, of the tuber-specific storage protein gene; the 23-kDa zein gene from maize; or the French bean beta-phaseolin gene), or pathogen-inducible promoters (for example, PR-1, prp-1 or beta-1,3 glucanase promoters, the fungal-inducible wirla promoter of wheat, and the nematode-inducible promoters, TobRB7-5A and Hmg-1, of tobacco and parsley, respectively).

Plant expression vectors may also optionally include RNA processing signals, e.g., introns, which have been shown to be important for efficient RNA synthesis and accumulation. The location of the RNA splice sequences can dramatically influence the level of transgene expression in plants. In, view of this fact, an intron may be positioned upstream or downstream of a nucleic acid molecule described herein in the transgene to modulate levels of gene expression.

In addition to the aforementioned 5' regulatory control sequences, the expression vectors may also include regulatory control regions which are generally present in the 3' regions of plant genes. For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide BASTA® (Hoechst A G, Frankfurt, Germany).

In addition, if desired, the plant expression construct may contain a modified or fully-synthetic nucleic acid molecule sequence which has been changed to enhance the performance of the gene in plants.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

The nucleic acid molecules herein described were cloned into the plasmid pEPT8. Plasmid pEPT8 is a derivative of pUC18 containing a plant expression cassette with the CaMV 35S promoter and terminator sequence which will allow the constructs to be constitutively expressed in the host plant. Following this step, the plant expression cassette is excised from plasmid pEPT8 and cloned into the binary plasmid pGA482G for transformation of host plants with the constructs of interest. Once potential constructs (e.g., concatenate constructs) have been constructed, each is tested for effectiveness against diverse GFLV strains in both laboratory and field settings.

Transient Assay for Determining the Effectiveness of the Concatenate Constructs

To identify candidate concatenate constructs with the most efficient anti-GFLV activity, a transient assay based on a model plant *Nicotiana benthamiana*, a systemic host of GFLV that is amenable to agroinfiltration, was used. *N. benthamiana* leaves were first infiltrated with *Agrobacterium tumefaciens* suspensions carrying GFLV-derived genetic constructs to mediate the transient expression of transgenes and eventually silencing. Then, agroinfiltrated plants were mechanically inoculated with GFLV and the anti-viral effects of concatenate constructs with silencing potential were measured by monitoring symptom development, if applicable, and investigating virus accumulation by a double antibody sandwich (DAS) enzyme-linked immunosorbent assays (ELISA) with GFLV-specific antibodies and reverse transcription (RT) polymerase chain reaction (PCR) assays with appropriate primers. Inhibition of viral multiplication was also confirmed by monitoring the production and accumulation of siRNA in agroinfiltrated leaves using standard Northern blotting procedures with total RNA enriched in small molecules and GFLV specific probes. Appropriate numbers of plant replicates were used for each construct tested. This transient assay provides a rapid screen to assess whether silencing is activated by GFLV genetic constructs and whether the constructs interfere with virus multiplication. The transient assay also provides a means for a rapid initial screen for resistance without the need for generating stable transformants for each construct, limiting the number of transgenic grapevine rootstocks events to be tested in naturally infected vineyards and accelerating the development of GFLV-resistant grapevine rootstocks of commercial value.

Figure 2:
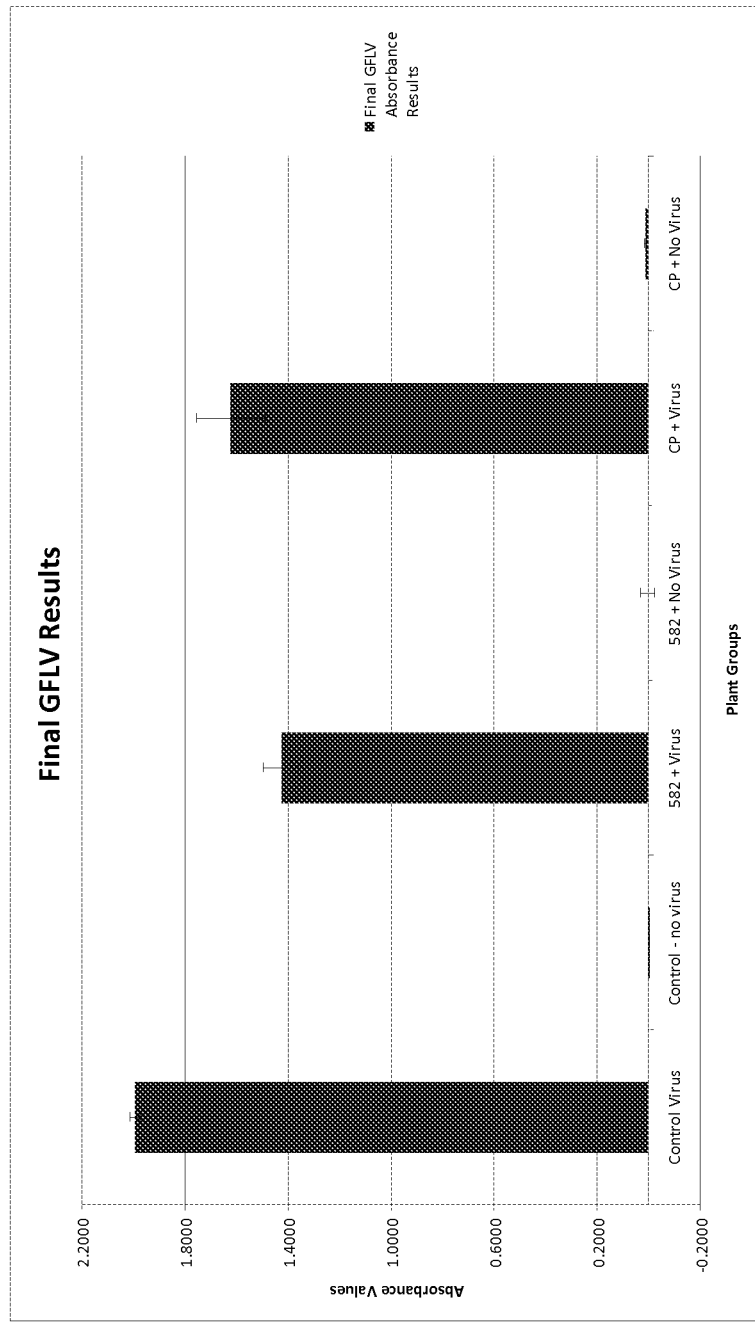
FIG. 2: Shows DAS-ELISA absorbance values for GFLV in *Nicotiana benthamiana* plants agro-infiltrated with i) no construct, ii) concatenate construct 582, or iii) a translatable coat protein (CP) gene construct. Plants were either mechanically inoculated with GFLV (Virus) or not (No virus).

The potential of concatenate construct 582 at interfering with GFLV multiplication was evaluated by using this transient assay. Results are shown in FIG. 2. DAS-ELISA absorbance values are shown for GFLV in *Nicotiana benthamiana* plants agro-infiltrated with concatenate construct 582 or a translatable coat protein (CP) gene construct. Plants were either mechanically inoculated with GFLV or not. A significant reduction in virus accumulation was observed in plants agroinfiltrated with concatenate construct 582 compared to controls. The reduction in virus accumulation was more pronounced for concatenate construct 582 than the translatable CP gene construct.

Grapevine Transformation

Generally, upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*), (2) the particle delivery system, (3) microinjection protocols, (4) polyethylene glycol (PEG) procedures, (5) liposome-mediated DNA uptake, (6) electroporation protocols, and (7) by vortexing. The method of transformation is not critical to the invention. Any method which provides for efficient transformation may be employed. Some exemplary methods for transforming grapes are found in Scorza et al. (Plant Cell Reports 14: 589 592, 1995), Baribault et al. (J. Expt. Bot. 41: 1045 1049, 1990), Mullins et al. (BioTechnology 8: 1041 1045, 1990), Nakano et al. (J. Expt. Bot. 45: 649 656, 1994), Kikkert et al. (Plant Cell Rep. 15: 311316, 1995), Krastanova et al. (Plant Cell Rep. 1: 550 554, 1995), Scorza et al. (Plant Cell Rep. 14: 589 592, 1994), Scorza et al. (J. Amer. Soc. Hort. Sci. 121: 616 619, 1996), Martinelli et al. (Theor Appl Genet. 88: 621628, 1994), and Legall et al. (Plant Sci. 102.

161170, 1994). As newer methods are available to transform plants or grapes or other host cells, they may be directly applied as well.

Suitable plants for use in the practice of the invention include, but are not limited to, grapevines (for example, *Vitis* spp., *Vitis* spp. hybrids, and all members of the subgenera *Euvitis* and *Muscadinia*), including scion or rootstock cultivars. Exemplary scion cultivars include, without limitation, those which are referred to as table or raisin grapes and those used in wine production such as Cabernet Franc, Cabernet Sauvignon, Chardonnay (for example, CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Other scion cultivars which can be used include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschct, Aligote, Alvarelhao, Aramon, Baco blanc (22A), Burger, Cabernet franc, Caberet, Sauvignon, Calzin, Carignan, Charbono, Chardonnay, Chasselas dore, Chemn blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon grin, Sauvignon vert, Scarlet, Seibel 5279, Seibel 9110, Seibel 13053, Semillon, Servant, Shiraz, Souzao, Sultana Crimson, Sylvaner, Tarmat, Teroldico, Tinta Madeira, Tinto cao, Touriga, Traminer, Trebbiano Toscano, Trousseau, Valdepenas, Viognier, Walschriesling, White Riesling, and Zinfandel.

Rootstock cultivars that are useful in the invention include, without limitation, *Vitis rupestris* Constantia, *Vitis rupestris* St. George, *Vitis california, Vitis girdiana, Vitis rotundifolia, Vitis rotundifolia* Carlos, Richter 110 (*Vitis berlandieri×rupestris*), 101-14 Millarder et de Grasset (*Vitis riparia×rupestris*), Teleki 5C (*Vitis berlandieri×riparia*), 3309 Couderc (*Vitis riparia×rupestris*), Riparia Gloire de Montpellier (*Vitis riparia*), 5BB Teleki (selection Kober, *Vitis berlandieri×riparia*), SO₄ (*Vitis berlandieri×rupestris*), 41B Millardet (*Vitis vinifera×berlandieri*), and 039-16 (*Vitis vinifera× Muscadinia*). Additional rootstock cultivars which can be used include Couderc 1202, Couderc 1613, Couderc 1616, Couderc 3309, Dog Ridge, Foex 33EM, Freedom, Ganzin 1 (A x R #1), Harmony, Kober 5BB, LN33, Millardet & de Grasset 41B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis california*, and *Vitis girdiana*.

In general, transfer and expression of transgenes in plant cells, including grape plants, are now routine practices to those skilled in the art, and have become major tools to carry out gene expression studies in plants and to produce improved plant varieties of agricultural or commercial interest.

Transgenic Grapevine Regeneration

Plant cells transformed with a plant expression vector can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are well known in the art.

In one particular example, a cloned sense translatable, sense nontranslatable (e.g., having an out-of-reading frame ATG including a stop codon after the initiation codon), or anti-sense nucleic acid molecule of the present invention under the control of the 35S CaMV promoter and the nopaline synthase terminator and carrying a selectable marker (for example, kanamycin resistance) is transformed into *Agrobacterium*. Transformation of grapevine with vector-containing *Agrobacterium* is carried out as described by Scorza and Cordts (Plant Cell Reports 14:589-592, 1995), which is hereby incorporated by reference. Putative transformants are selected after a few weeks on plant tissue culture media containing kanamycin. Kanamycin-resistant plant material is then placed on plant tissue culture media without hormones for root initiation.

Transgenic plants expressing the selectable marker are then screened for transmission of the transgene by standard detection techniques as described above. Each positive transgenic plant and its transgenic progeny are unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include Northern blot assays and nuclear run-off assays. The RNA-positive plants are then analyzed for resistance to GFLV infection using standard methods. Transformed grapevines that express a sense nontranslatable sequence having resistance to fanleaf disease relative to control plants are taken as being useful in the invention.

Transformation Protocol

The following transformation protocol was used to produce transgenic grapevine rootstocks expressing concatenate constructs. Transgenic grapevine rootstocks expressing concatenate constructs were obtained by *Agrobacterium tumefaciens*-mediated transformation of somatic embryogenic cultures. Embryogenic cultures were initiated from immature anthers of 3309 Couderc (*V. riparia×V. rupestris*), 101-14 Millardet et De Grasset (*V. riparia×V. rupestris*), *V. rupestris* St. George, 110 Richter (*V. rupestris×V. berlandieri*), and SO4 (*V. berlandieri×V. riparia*). Isolated anthers were cultured on Murashige and Skoog (MS) medium supplemented with 0.2% sucrose, 0.2 mg/l benzylaminopurinc (BA), 1.1 mg/l 2,4-dichlorophenoxyacetic acid, and 7.2 g/l Noble agar at 28° C. in the dark. This medium is referred to as embryo induction medium (EIM). Sub-culturing of primary calli was done at 3-4 week intervals. Disarmed *A. tumefaciens* strain C58Z707 harboring binary plasmids with concatenate constructs were used for transformation of embryogenic calli by cultivation on EIM containing 100 mg/l acetosyringone at 25° C. in the dark for a 48 hour co-culture. Then, embryogenic calli were transferred on embryo induction medium supplemented with 300 mg/l cefotaxime, 200 mg/l carbenicilin, 100 mg/l acetosyringone, and 25 mg/l kanamycin, and cultured at 28° C. in the dark. Clusters of secondary embryogenic calli with developing embryos were obtained by transfer of primary embryogenic calli on half strength MS medium supplemented with embryo differentiation medium (EDM; 10 g/l sucrose, 3.6 ml/l glycerol, and 7.2 g/l Noble agar). This medium is referred to as Cultures were maintained at 28° C. in the dark over one to two months with sub-cultures at 3-week intervals. Embryo germination and growth was achieved by transferring embryogenic clusters with differentiated embryos on full strength MS with embryo elongation medium (EEM; 20 g/l sucrose, 3.6 ml/l glycerol, 1 g/l casein hydrolysat, and 7.2 g/l Noble agar). Cultures were grown in the dark at 28° C. with sub-cultures every three weeks for one-two months. Elongated embryos (5-15 mm in length) were transferred onto embryo regeneration medium (ERM; woody plant medium without vitamins but supplemented with 0.1 mg/l BA, 3 g/l activated charcoal, 1.5% sucrose, and 7.2 g/l Noble agar) for plant regeneration. Elongated embryos were maintained at 25° C. with a 16:8 hour (light:dark) photoperiod under cool fluorescent light at 45 μm-2s-1 in a tissue culture room. Plantlets derived from germinating embryos will be propagated as single node cuttings on ERM in baby food jars for multiplication and rooting under cool fluorescent light at 45 μm-2s-1 in a tissue culture room. After 2-4 weeks, rooted plantlets were potted into Cornell mix (a mixture of peat, vermiculite, ground limestone and uni-mix 10-20-5) and grown at 25±5° C. with a 16:8 hour (light:dark) photoperiod in a greenhouse. A total of 12 independent lines of rootstock 3309C and 6 independent lines of rootstock SO4 expressing concatenate constructs 582 and 714 were produced using the above protocol.

Transgenic Grapevine Resistance Evaluation

The resistance of transgenic grapevines to GFLV infection can be evaluated, for example, in a naturally GFLV-infected vineyard site. Resistance can be tested, for example, by visual monitoring of symptom development, assessing plant vigor, and determining virus accumulation over time using rt-PCR or a double antibody sandwich (DAS) enzyme-linked immunosorbent assays (ELISA), or by measurement of food production provided that rootstocks are grafted with scions material. Exemplary methods for evaluating grapevine resistance to viral infection are given in Vigne et al. (Transgenic Res. 13:165-173), Komar et al. (Plant Disease 92:1689-1694), and Valat et al. (Plant Science 170:739-747), each of which are hereby incorporated by reference.

Field Testing

Mature grape plants transformed the constructs of the present invention can be tested under field conditions in virus (e.g., GFLV) infested vineyards (i.e., plots of land which includes three or more transgenic grapevines or grapevine components which express any of the nucleic acid molecules or vectors described herein) in any suitable location such as, for example, Chile, California, or France according to standard methods.

Food Products

In some aspects, the invention features products derived from plants transformed with the above-described nucleic acid molecules. Foodstuffs products derived from grape plants include grape fruits (e.g., black, blue, blue-black, golden, red, green, purple, and white colors in seeded and seedless varieties). Common varieties of grapes include Thompson, Flame, Ruby, Perlette and Tokay grapes. Additional grape foodstuffs include raisins (dried grapes), jellys, and jams. Beverages derived from grapes include wines and juices. Varieties of wine include Pinot Noir, Merlot, Chardonnay, and Cabernet Sauvignon. Many wines are known by tradename, or are named by the regions in which they are grown (e.g., Bordeaux and Chianti).

Additional food products of the present invention include those derived from grape, raspberry, strawberry, cherry, hop, black currant, currant, elder, rhubarb, lettuce, tomato, cucumber, celery, daffodil and forsythia. Common uses of these plants in foodstuffs are well known in the art. These include fruits, jams, jellys, salads, beer, juices, cakes, ice cream, sauces, cookies, and the like.

All publications and patent applications mentioned in this specification are herein incorporated by reference to the same extent as if each independent publication or patent application was specifically and individually indicated to be incorporated by reference.

What is claimed is:

1. A substantially purified nucleic acid molecule comprising a sequence selected from the group consisting of SEQ ID NO:17 (concatenate 463), SEQ ID NO:18 (concatenate 582), SEQ ID NO:19 (concatenate 714), SEQ ID NO:20 (concatenate 678), SEQ ID NO:21 (concatenate 123), SEQ ID NO:22 (concatenate construct 375), SEQ ID NO:23 (concatenate 168), SEQ ID NO:24 (concatenate 245), SEQ ID NO:25 (concatenate 12367845), and SEQ ID NO:26 (concatenate 375168).

2. The nucleic acid molecule of claim 1, said nucleic acid molecule conferring resistance to a plant pathogen on a plant expressing said nucleic acid molecule.

3. The nucleic acid molecule of claim 1, wherein said nucleic acid molecule is operably linked to a promoter.

4. The nucleic acid molecule of claim 3, wherein the promoter is a developmentally-regulated, organelle-specific, tissue-specific, constitutive or cell-specific promoter.

5. The nucleic acid molecule of claim 3, wherein said promoter is inducible by one or more external agents.

6. The nucleic acid molecule of claim 1, wherein said nucleic acid molecule is DNA.

7. The nucleic acid molecule of claim 1, wherein said nucleic acid molecule is RNA.

8. A vector comprising the nucleic acid molecule of claim 1.

9. A vector comprising the nucleic acid molecule of claim 1, wherein the nucleic acid molecule is operably linked, in a sense-translatable, sense-nontranslatable, or an anti-sense orientation, to a promoter.

10. A cell comprising the vector of claim 8 or 9.

11. The cell of claim 10, wherein said cell is a bacterial, insect, mammalian, or a plant cell.

12. A plant or plant component comprising the nucleic acid molecule of claim 1.

13. A plant or plant component comprising the vector of claim 8 or 9.

14. The plant or plant component of claim 13, wherein said plant is a dicot.

15. The plant or plant component of claim 14, wherein said dicot is a grape plant.

16. The plant or plant component of claim 15, wherein said grape plant is a member of the genus *Vitis*.

17. The plant or plant component of claim 15, wherein said plant component is a grape, somatic embryo, a scion, or a rootstock.

18. A method of enhancing resistance to a grapevine fanleaf virus in a plant, said method comprising:
(a) providing a plant cell that expresses the nucleic acid molecule of claim 1; and
(b) regenerating a plant or plant component from said plant cell, wherein said nucleic acid is expressed in said plant, and wherein said plant has enhanced resistance to a plant pathogen compared to a corresponding untransformed plant.

19. The method of claim 18, wherein said plant is a dicot.

20. The method of claim 19, wherein said dicot is a grape plant.

21. The method of claim 20, wherein said grape plant is a member of the genus *Vitis*.

22. The method of claim 20, wherein said plant component is a grape, somatic embryo, a scion, or a rootstock.

23. A method for increasing resistance to viral disease in a grape plant cell, said method comprising transforming said grape plant cell with a nucleic acid molecule according to claim 1, wherein expression of said nucleic acid in said grape plant cell increases resistance of said grape plant cell to viral disease.

24. The method of claim 23, further comprising propagating a grape plant from said plant cell.

25. The method of claim 23, wherein said plant cell is a scion cell.

26. The method of claim 23, wherein said plant cell is a rootstock cell.

27. The method of claim 23, wherein said viral disease is grapevine fanleaf disease.

28. A grape plant comprising a nucleic acid molecule according to claim 1, wherein expression of said nucleic acid in said grape plant cell increases resistance of said grape plant cell to viral disease.

29. The plant of claim 28, wherein said plant is a scion cultivar.

30. The plant of claim 28, wherein said plant is a rootstock cultivar.

31. The plant of claim 28, wherein said viral disease is grapevine fanleaf disease.

32. A grape plant tissue wherein a cell of said tissue comprises a nucleic acid molecule according to claim 1, wherein expression of the nucleic acid molecule in said grape plant cell increases resistance of said grape plant cell to viral disease.

33. The grape plant tissue of claim 32, wherein said plant tissue is a scion, a rootstock, a seed, or a somatic embryo.

34. The grape plant tissue of claim 33, wherein said viral disease is grapevine fanleaf disease.

35. The method according to claim 34, wherein said grapevine fanleaf disease is caused by a grapevine fanleaf virus.

* * * * *

SEQUENCE LISTING

```
<160> NUMBER OF SEQ ID NOS: 28

<210> SEQ ID NO 1
<211> LENGTH: 204
<212> TYPE: DNA
<213> ORGANISM: Artificial Sequence
<220> FEATURE:
<223> OTHER INFORMATION: Synthetic Construct

<400> SEQUENCE: 1
ggtaccagat gaattgtgct ttccatatcc tgatcctaag cagcccgcca tccttagcgc      60
agaggatgaa cgccttaagg gaacgatcca tgaaggatac actccgttaa gggatggcat     120
gaagaagttt gctgagccaa tgtatctgct agaggaaaaa ctactcgatg aagttgcagg     180
tgacatggtt cagacgtggt atga                                            204
```

<210> SEQ ID NO 2
<211> LENGTH: 196
<212> TYPE: DNA
<213> ORGANISM: Artificial Sequence
<220> FEATURE:
<223> OTHER INFORMATION: Synthetic Construct

<400> SEQUENCE: 2
cttgttgaga gtaaaatttt tgtcttttc ccgcctactg atgaagaaga gaggccacct    60
gccttgtcaa gtgggcatca atccttatag tcgcgaatgg accgatttgt atcaccgctt   120
aggtgaactc tctgatgtcg gatacaattg tgattataag gcttttgatg gcctaattac   180
ggagcaaatt ttgagt                                                   196

<210> SEQ ID NO 3
<211> LENGTH: 333
<212> TYPE: DNA
<213> ORGANISM: Artificial Sequence
<220> FEATURE:
<223> OTHER INFORMATION: Synthetic Construct

<400> SEQUENCE: 3
tacctatggt gatgataatg tcttcactgt ggcacaatct gtcatgcagt attttactgg    60
cgatgctctg aaaatgcaaa tggcaaagct tggggtaact attactgatg ggaaagataa   120
gtctctttcc actattccag cccgtccact gctggaatta gagttttga aacgtggatt    180 tgttagaagc tctgggggta tgataaatgc gcctttggaa aaattatcaa taatgagttc   240
tttggtctac atcagaagtg atggctcaga catgttgcag aaactattgg acaatgttaa   300
tactgcactt gtcgagcttt atctacatgg tga                                333

<210> SEQ ID NO 4
<211> LENGTH: 131
<212> TYPE: DNA
<213> ORGANISM: Artificial Sequence
<220> FEATURE:
<223> OTHER INFORMATION: Synthetic Construct

<400> SEQUENCE: 4
ccccagctcc ctactttagg gctgttgggg cttttgcacc aacccggtcc gagtttgttc    60
gggccattgt ggaaaggctc acccggctac gggaggagtc gagagctgcg gcactctttg   120
ccgaattgcc a                                                        131

<210> SEQ ID NO 5
<211> LENGTH: 160
<212> TYPE: DNA
<213> ORGANISM: Artificial Sequence
<220> FEATURE:
<223> OTHER INFORMATION: Synthetic Construct

<400> SEQUENCE: 5
tgatagaaac gttgatcttc ctcaacttga ggctgagccc agactgagct caaccgtgag    60
agggctagcc ggcagaggag taatctacat tcccaaggat tgccaggcaa atagatactt   120
gggcaccctg aatatacgtg atatgatctc agacttcaag                         160

<210> SEQ ID NO 6
<211> LENGTH: 146
<212> TYPE: DNA
<213> ORGANISM: Artificial Sequence
<220> FEATURE:
<223> OTHER INFORMATION: Synthetic Construct

<400> SEQUENCE: 6

```
ttagtgagtg aacgggacc actatggact ggaatgaact ttttaagtat cccggggtgt      60
atgtggaaga ggacggaagt tttgaagtaa agattcgctc tccatatcac cgaactcctg    120
ccagattgct tgctggtcaa agtcag                                          146
```

<210> SEQ ID NO 7
<211> LENGTH: 115
<212> TYPE: DNA
<213> ORGANISM: Artificial Sequence
<220> FEATURE:
<223> OTHER INFORMATION: Synthetic Construct

<400> SEQUENCE: 7

```
agaagaaatt gagattggtt ctcgtttctt cgatttcact tcgaatactt gtagggtatc     60
tatgggtgaa aatccgtttg ctgcaatgat tgcctgccat ggattgcata gtggt         115
```

<210> SEQ ID NO 8
<211> LENGTH: 252
<212> TYPE: DNA
<213> ORGANISM: Artificial Sequence
<220> FEATURE:
<223> OTHER INFORMATION: Synthetic Construct

<400> SEQUENCE: 8

```
tttagctttt atggtagaac cagtttccca gtctagtgat acgtagatat ctagggtatc     60
tgactttaaa agacccaagt gtatatatgt gttttgtcag tagcatgtat tattttgtgt    120
tataatttgt tttaacttgt tttccgcttt tgtgtgttta gtttcatgct tttagtggcg    180
acagtgtgtt gtttgtcctt tggacacact tgcctagttg gacgcaaaaa gattttttcct  240
ttcttttttac tg                                                        252
```

<210> SEQ ID NO 9
<211> LENGTH: 666
<212> TYPE: DNA
<213> ORGANISM: Artificial Sequence
<220> FEATURE:
<223> OTHER INFORMATION: Synthetic Construct

<400> SEQUENCE: 9

```
gagcggccgc tccggacccc agctccctac tttagggctg ttggggcttt tgcaccaacc     60
cggtccgagt tgttcgggc cattgtggaa aggctcaccc ggctacggga ggagtcgaga    120
gctgcggcac tctttgccga attgccaggg cccttagtga gtggaacggg accactatgg   180
actggaatga actttttaag tatcccgggg tgtatgtgga agaggacgga agttttgaag   240
taaagattcg ctctccatat caccgaactc ctgccagatt gcttgctggt caaagtcagg   300
cggccgctct agcgtcgact acctatggtg atgataatgt cttcactgtg gcacaatctg   360
tcatgcagta ttttactggc gatgctctga aaatgcaaat ggcaaagctt ggggtaacta   420
ttactgatgg gaaagataag tctctttcca ctattccagc ccgtccactg ctggaattag   480
agttttttgaa acgtggattt gttagaagct ctggggtat gataaatgcg cctttggaaa    540
aattatcaat aatgagttct tggtctaca tcagaagtga tggctcagac atgttgcaga    600
aactattgga caatgttaat actgcacttg tcgagcttta tctacatggt gactcgagac   660
cggttc                                                               666
```

<210> SEQ ID NO 10
<211> LENGTH: 664
<212> TYPE: DNA

<213> ORGANISM: Artificial Sequence
<220> FEATURE:
<223> OTHER INFORMATION: Synthetic Construct

<400> SEQUENCE: 10

| | |
|---|---|
| gagcggccgc tccggatgat agaaacgttg atcttcctca acttgaggct gagcccagac | 60 |
| tgagctcaac cgtgagaggg ctagccggca gaggagtaat ctacattccc aaggattgcc | 120 |
| aggcaaatag atacttgggc accctgaata tacgtgatat gatctcagac ttcaaggggc | 180 |
| cctttagctt ttatggtaga accagtttcc cagtctagtg atacgtagat atctagggta | 240 |
| tctgacttta aaagacccaa gtgtatatat gtgttttgtc agtagcatgt attattttgt | 300 |
| gttataattt gttttaactt gttttccgct tttgtgtgtt tagtttcatg cttttagtgg | 360 |
| cgacagtgtg ttgtttgtcc tttgacaca cttgcctagt tggacgcaaa aagatttttc | 420 |
| cttcttttt actggcggcc gctctagcgt cgaccttgtt gagagtaaaa ttttgtctt | 480 |
| tttcccgcct actgatgaag aagagaggcc acctgccttg tcaagtgggc atcaatcctt | 540 |
| atagtcgcga atggaccgat tgtatcacc gcttaggtga actctctgat gtcggataca | 600 |
| attgtgatta taaggctttt gatggcctaa ttacggagca aattttgagt ctcgagaccg | 660 |
| gttc | 664 |

<210> SEQ ID NO 11
<211> LENGTH: 508
<212> TYPE: DNA
<213> ORGANISM: Artificial Sequence
<220> FEATURE:
<223> OTHER INFORMATION: Synthetic Construct

<400> SEQUENCE: 11

| | |
|---|---|
| gagccggcgg gcccagaaga aattgagatt ggttctcgtt tcttcgattt cacttcgaat | 60 |
| acttgtaggg tatctatggg tgaaaatccg tttgctgcaa tgattgcctg ccatggattg | 120 |
| catagtggtg cggccgctct agcgtcgacg gtaccagatg aattgtgctt tccatatcct | 180 |
| gatcctaagc agcccgccat ccttagcgca gaggatgaac gccttaaggg aacgatccat | 240 |
| gaaggataca ctccgttaag ggatggcatg aagaagtttg ctgagccaat gtatctgcta | 300 |
| gaggaaaaac tactcgatga agttgcaggt gacatggttc agacgtggta tgactcgaga | 360 |
| ccggaccccca gctccctact ttagggctgt tgggcttttt gcaccaaccc ggtccgagtt | 420 |
| tgttcgggcc attgtggaaa ggctcacccg gctacgggag gagtcgagag ctgcggcact | 480 |
| ctttgccgaa ttgccagggc ccactagt | 508 |

<210> SEQ ID NO 12
<211> LENGTH: 557
<212> TYPE: DNA
<213> ORGANISM: Artificial Sequence
<220> FEATURE:
<223> OTHER INFORMATION: Synthetic Construct

<400> SEQUENCE: 12

| | |
|---|---|
| gagccggcgg gcccttagtg agtggaacgg gaccactatg gactggaatg aacttttaa | 60 |
| gtatcccggg gtgtatgtgg aagaggacgg aagttttgaa gtaaagattc gctctccata | 120 |
| tcaccgaact cctgccagat tgcttgctgg tcaaagtcag gcggcccaga agaaattgag | 180 |
| attggttctc gtttcttcga tttcacttcg aatacttgta gggtatctat gggtgaaaat | 240 |
| ccgtttgctg caatgattgc ctgccatgga ttgcatagtg gtgcggccct ttagctttta | 300 |
| tggtagaacc agtttcccag tctagtgata cgtagatatc tagggtatct gactttaaaa | 360 |

| gacccaagtg tatatatgtg tttttgtcagt agcatgtatt attttgtgtt ataatttgtt | 420 |
| ttaacttgtt ttccgctttt gtgtgtttag tttcatgctt ttagtggcga cagtgtgttg | 480 |
| tttgtccttt ggacacactt gcctagttgg acgcaaaaag atttttcctt tctttttact | 540 |
| ggcggccgct ctagatc | 557 |

<210> SEQ ID NO 13
<211> LENGTH: 773
<212> TYPE: DNA
<213> ORGANISM: Artificial Sequence
<220> FEATURE:
<223> OTHER INFORMATION: Synthetic Construct

<400> SEQUENCE: 13

| gagctagcgt cgacggtacc agatgaattg tgctttccat atcctgatcc taagcagccc | 60 |
| gccatcctta gcgcagagga tgaacgcctt aagggaacga tccatgaagg atacactccg | 120 |
| ttaagggatg gcatgaagaa gtttgctgag ccaatgtatc tgctagagga aaaactactc | 180 |
| gatgaagttg caggtgacat ggttcagacg tggtatgact cgaccttgtt gagagtaaaa | 240 |
| ttttttgtctt tttcccgcct actgatgaag aagagaggcc acctgccttg tcaagtgggc | 300 |
| atcaatcctt atagtcgcga atggaccgat ttgtatcacc gcttaggtga actctctgat | 360 |
| gtcggataca attgtgatta taaggctttt gatggcctaa ttacggagca aattttgagt | 420 |
| ctcgactacc tatggtgatg ataatgtctt cactgtggca caatctgtca tgcagtattt | 480 |
| tactggcgat gctctgaaaa tgcaaatggc aaagcttggg gtaactatta ctgatgggaa | 540 |
| agataagtct ctttccacta ttccagcccg tccactgctg gaattagagt ttttgaaacg | 600 |
| tggatttgtt agaagctctg ggggtatgat aaatgcgcct ttggaaaaat tatcaataat | 660 |
| gagttctttg gtctacatca gaagtgatgg ctcagacatg ttgcagaaac tattggacaa | 720 |
| tgttaatact gcacttgtcg agctttatct acatggtgac tcgagaccgg ttc | 773 |

<210> SEQ ID NO 14
<211> LENGTH: 668
<212> TYPE: DNA
<213> ORGANISM: Artificial Sequence
<220> FEATURE:
<223> OTHER INFORMATION: Synthetic Construct

<400> SEQUENCE: 14

| gagctagcgt cgactaccta tggtgatgat aatgtcttca ctgtggcaca atctgtcatg | 60 |
| cagtatttta ctggcgatgc tctgaaaatg caaatggcaa agcttggggt aactattact | 120 |
| gatgggaaag ataagtctct ttccactatt ccagcccgtc cactgctgga attagagttt | 180 |
| ttgaaacgtg gatttgttag aagctctggg gtatgataa atgcgccttt ggaaaaatta | 240 |
| tcaataatga gttctttggt ctacatcaga agtgatggct cagacatgtt gcagaaacta | 300 |
| ttggacaatt taatactgc acttgtcgag ctttatctac atggtgactc gagaccggcg | 360 |
| ggcccagaag aaattgagat tggttctcgt ttcttcgatt tcacttcgaa tacttgtagg | 420 |
| gtatctatgg gtgaaaatcc gtttgctgca atgattgcct gccatggatt gcatagtggt | 480 |
| gcggccgctc cggatgatag aaacgttgat cttcctcaac ttgaggctga gcccagactg | 540 |
| agctcaaccg tgagagggct agccggcaga ggagtaatct acattcccaa ggattgccag | 600 |
| gcaaatagat acttgggcac cctgaatata cgtgatatga tctcagactt caaggggccc | 660 |
| actagttc | 668 |

<210> SEQ ID NO 15

```
<211> LENGTH: 657
<212> TYPE: DNA
<213> ORGANISM: Artificial Sequence
<220> FEATURE:
<223> OTHER INFORMATION: Synthetic Construct

<400> SEQUENCE: 15
gagctagcgt cgacggtacc agatgaattg tgctttccat atcctgatcc taagcagccc      60
gccatcctta gcgcagagga tgaacgcctt aagggaacga tccatgaagg atacactccg     120
ttaagggatg gcatgaagaa gtttgctgag ccaatgtatc tgctagagga aaaactactc     180
gatgaagttg caggtgacat ggttcagacg tggtatgact cgagaccggc gggcccttag     240
tgagtggaac gggaccacta tggactggaa tgaactttt aagtatcccg gggtgtatgt     300
ggaagaggac ggaagttttg aagtaaagat tcgctctcca tatcaccgaa ctcctgccag     360
attgcttgct ggtcaaagtc aggcggccct ttagctttta tggtagaacc agtttcccag     420
tctagtgata cgtagatatc tagggtatct gactttaaaa gacccaagtg tatatatgtg     480
ttttgtcagt agcatgtatt attttgtgtt ataatttgtt ttaacttgtt ttccgctttt     540
gtgtgtttag tttcatgctt ttagtggcga cagtgtgttg tttgtccttt ggacacactt     600
gcctagttgg acgcaaaaag attttcctt tcttttact ggcggccgct ctagatc         657

<210> SEQ ID NO 16
<211> LENGTH: 540
<212> TYPE: DNA
<213> ORGANISM: Artificial Sequence
<220> FEATURE:
<223> OTHER INFORMATION: Synthetic Construct

<400> SEQUENCE: 16
gagctagcgt cgaccttgtt gagagtaaaa ttttgtctt tttcccgcct actgatgaag      60
aagagaggcc acctgccttg tcaagtgggc atcaatcctt atagtcgcga atggaccgat    120
ttgtatcacc gcttaggtga actctctgat gtcggataca attgtgatta taaggctttt    180
gatggcctaa ttacggagca aatttttgagt ctcgagaccg gaccccagct ccctacttta   240
gggctgttgg ggcttttgca ccaacccggt ccgagtttgt tcgggccatt gtggaaaggc    300
tcacccggct acgggaggag tcgagagctg cggcactctt tgccgaattg ccagggccgc    360
tccggatgat agaaacgttg atcttcctca acttgaggct gagcccagac tgagctcaac    420
cgtgagaggg ctagccggca gaggagtaat ctacattccc aaggattgcc aggcaaatag    480
atacttgggc accctgaata tacgtgatat gatctcagac ttcaaggggc ccactagttc    540

<210> SEQ ID NO 17
<211> LENGTH: 647
<212> TYPE: DNA
<213> ORGANISM: Artificial Sequence
<220> FEATURE:
<223> OTHER INFORMATION: Synthetic Construct

<400> SEQUENCE: 17 ggatccccc agctccctac tttagggctg ttggggcttt tgcaccaacc cggtccgagt      60 tgttcgggc cattgtggaa aggctcaccc ggctacggga ggagtcgaga gctgcggcac    120
tctttgccga attgccaggg cccttagtga gtggaacggg accactatgg actgaatga     180 acttttaag tatcccgggg tgtatgtgga agaggacgga agttttgaag taaagattcg    240
ctctccatat caccgaactc ctgccagatt gcttgctggt caaagtcagg cggccgctct    300
agcgtcgact acctatggtg atgataatgt cttcactgtg gcacaatctg tcatgcagta    360
```

| | |
|---|---|
| ttttactggc gatgctctga aaatgcaaat ggcaaagctt ggggtaacta ttactgatgg | 420 |
| gaaagataag tctctttcca ctattccagc ccgtccactg ctggaattag agtttttgaa | 480 |
| acgtggattt gttataagct ctgggggtat gataaatgcg cctttggaaa aattatcaat | 540 |
| aatgagttct ttggtctaca tcagaagtga tggctcagac ctgttgcaga aactattgga | 600 |
| cagtgttaat actgcacttg tccagctttt ctagctggtg aggatcc | 647 |

<210> SEQ ID NO 18
<211> LENGTH: 646
<212> TYPE: DNA
<213> ORGANISM: Artificial Sequence
<220> FEATURE:
<223> OTHER INFORMATION: Synthetic Construct

<400> SEQUENCE: 18

| | |
|---|---|
| ggatcctgat agaaacgttg atcttcctca acttgaggct gagcccagac tgagctcaac | 60 |
| cgtgagaggg ctagccggca gaggagtaat ctacattccc aaggattgcc aggcaaatag | 120 |
| atacttgggc accctgaata cgtgatat gatctcagac ttcaaggggc cctttagctt | 180 |
| ttatggtaga accagtttcc cagtctagta tacgtagat atctagggta tctgacttta | 240 |
| aaagacccaa gtgtatatat gtgttttgtc agtagcatgt attattttgt gttataattt | 300 |
| gttttaactt gttttccgct tttgtgtgtt tagtttcatg cttttagtgg cgacagtgtg | 360 |
| ttgtttgtcc tttggacaca cttgcctagt tggacgcaaa aagattttc ctttcttttt | 420 |
| actggcggcc gctctagcgt cgaccttgtt gagagtaaaa tttttgtctt tttcccgcct | 480 |
| actgatgaag aagagaggcc acctgccttg tcaagtgggc atcaatcctt atagtcgcga | 540 |
| atggaccgat ttgtatcacc gcttaggtga actctctgat gtcggataca attgtgatta | 600 |
| taaggctttt gatggcctaa ttacggagca aattttgagt ggatcc | 646 |

<210> SEQ ID NO 19
<211> LENGTH: 494
<212> TYPE: DNA
<213> ORGANISM: Artificial Sequence
<220> FEATURE:
<223> OTHER INFORMATION: Synthetic Construct

<400> SEQUENCE: 19

| | |
|---|---|
| ggatccagaa gaaattgaga ttggttctcg tttcttcgat ttcacttcga atacttgtag | 60 |
| ggtatctatg ggtgaaaatc cgtttgctgc aatgattgcc tgccatggat tgcatagtgg | 120 |
| tgcggccgct ctagcgtcga cggtaccaga tgaattgtgc tttccatatc ctgatcctaa | 180 |
| gcagcccgcc atccttagcg cagaggatga acgccttaag gaacgatcc atgaaggata | 240 |
| cactccgtta agggatggca tgaagaagtt tgctgagcca atgtatctgc tagaggaaaa | 300 |
| actactcgat gaagttgcag gtgacatggt tcagacgtgg tatgactcga gaccggaccc | 360 |
| cagctcccta ctttagggct gttggggctt ttgcaccaac ccggtccgag tttgttcggg | 420 |
| ccattgtgga aaggctcacc cggctacggg aggagtcgag agctgcggca ctctttgccg | 480 |
| aattgccagg atcc | 494 |

<210> SEQ ID NO 20
<211> LENGTH: 539
<212> TYPE: DNA
<213> ORGANISM: Artificial Sequence
<220> FEATURE:
<223> OTHER INFORMATION: Synthetic Construct

<400> SEQUENCE: 20

```
ggatccttag tgagtggaac gggaccacta tggactggaa tgaacttttt aagtatcccg    60
gggtgtatgt ggaagaggac ggaagttttg aagtaaagat tcgctctcca tatcaccgaa   120
ctcctgccag attgcttgct ggtcaaagtc aggcggccca aagaaattg agattggttc    180 tcgtttcttc gatttcactt cgaatacttg tagggtatct atgggtgaaa atccgtttgc   240
tgcaatgatt gcctgccatg gattgcatag tggtgcggcc ctttagcttt tatggtagaa   300
ccagtttccc agtctagtga tacgtagata tctagggtat ctgactttaa aagacccaag   360
tgtatatatg tgttttgtca gtagcatgta ttattttgtg ttataatttg ttttaacttg   420
ttttccgctt ttgtgtgttt agtttcatgc ttttagtggc gacagtgtgt tgtttgtcct   480
ttggacacac ttgcctagtt ggacgcaaaa agattttttc tttctttta ctgggatcc     539

<210> SEQ ID NO 21
<211> LENGTH: 757
<212> TYPE: DNA
<213> ORGANISM: Artificial Sequence
<220> FEATURE:
<223> OTHER INFORMATION: Synthetic Construct

<400> SEQUENCE: 21
ggatccggta ccagatgaat tgtgctttcc atatcctgat cctaagcagc ccgccatcct    60
tagcgcagag gatgaacgcc ttaagggaac gatccatgaa ggatacactc cgttaaggga   120
tggcatgaag aagtttgctg agccaatgta tctgctagag gaaaaactac tcgatgaagt   180
tgcaggtgac atggttcaga cgtggtatga ctcgaccttg ttgagagtaa aattttgtc    240 ttttcccgc ctactgatga agaagagagg ccacctgcct tgtcaagtgg gcatcaatcc   300
ttatagtcgc gaatggaccg atttgtatca ccgcttaggt gaactctctg atgtcggata   360
caattgtgat tataaggctt ttgatggcct aattacggag caaattttga gtctcgacta   420
cctatggtga tgataatgtc ttcactgtgg cacaatctgt catgcagtat tttactggcg   480
atgctctgaa aatgcaaatg gcaaagcttg gggtaactat tactgatggg aaagataagt   540
ctctttccac tattccagcc cgtccactgt ggaattaga gttttgaaa cgtggatttg    600 ttagaagctc tggggtatg ataaatgcgc ctttggaaaa attatcaata atgagttct    660 tggtctacat cagaagtgat ggctcagaca tgttgcagaa actattggac aatgttaata   720
ctgcacttgt cgagctttat ctacatggtg aggatcc                            757

<210> SEQ ID NO 22
<211> LENGTH: 653
<212> TYPE: DNA
<213> ORGANISM: Artificial Sequence
<220> FEATURE:
<223> OTHER INFORMATION: Synthetic Construct

<400> SEQUENCE: 22
ggatcctacc tatggtgatg ataatgtctt cactgtggca caatctgtca tgcagtattt    60
tactggcgat gctctgaaaa tgcaaatggc aaagcttggg gtaactatta ctgatgggaa   120
agataagtct ctttccacta ttccagcccg tccactgctg aattagagt tttgaaacg    180 tggatttgtt agaagctctg ggggtatgat aaatgcgcct ttggaaaaat tatcaataat   240
gagttctttg gtctacatca gaagtgatgg ctcagacatg ttgcagaaac tattggacaa   300
tgttaatact gcacttgtcg agctttatct acatggtgac tcgagaccgg cgggcccaga   360
ataaattgag attggttctc gtttcttcga tttcacttcg aatacttgta gggtatctat   420
gggtgaaaat ccgtttgctg caatgattgc ctgccatgga ttgcatagtg gtgcggccgc   480
```

```
tccggatgat agaaatcgtt gatcttcctc aacttgaggc tgagcccaga ctgacctcaa    540
ccgtgagagg gctagccggc aaaggagtaa tctactttcc caaggattgc caggcaaata    600
gatacttggc caccctgaat atacgtgata tgatctcaga cttcaaggga tcc           653
```

<210> SEQ ID NO 23
<211> LENGTH: 639
<212> TYPE: DNA
<213> ORGANISM: Artificial Sequence
<220> FEATURE:
<223> OTHER INFORMATION: Synthetic Construct

<400> SEQUENCE: 23

```
ggatccggta ccagatgaat tgtgctttcc atatcctgat cctaagcagc ccgccatcct     60
tagcgcagag gatgaacgcc ttaagggaac gatccatgaa ggatacactc cgttaaggga    120
tggcatgaag aagtttgctg agccaatgta tctgctagag gaaaaactac tcgatgaagt    180
tgcaggtgac atggttcaga cgtggtatga ctcgagaccg gcgggccctt agtgagtgga    240
acgggaccac tatggactgg aatgaacttt ttaagtatcc cggggtgtat gtggaagagg    300
acggaagttt tgaagtaaag attcgctctc catatcaccg aactcctgcc agattgcttg    360
ctggtcaaag tcaggcggcc ctttagcttt tatggtagaa ccagtttccc agtctagtga    420
tacgtagata tctagggtat ctgactttaa aagacccaag tgtatatatg tgttttgtca    480
gtagcatgta ttattttgtg ttataatttg ttttaacttg ttttccgctt tgtgtgtttt    540
agtttcatgc ttttagtggc gacagtgtgt tgtttgtcct ttggacacac ttgcctagtt    600
ggacgcaaaa agatttttcc tttcttttta ctgggatcc                          639
```

<210> SEQ ID NO 24
<211> LENGTH: 524
<212> TYPE: DNA
<213> ORGANISM: Artificial Sequence
<220> FEATURE:
<223> OTHER INFORMATION: Synthetic Construct

<400> SEQUENCE: 24

```
ggatcccttg ttgagagtaa aattttttgtc tttttcccgc ctactgatga agaagagagg    60
ccacctgcct tgtcaagtgg gcatcaatcc ttatagtcgc gaatggaccg atttgtatca   120
ccgcttaggt gaactctctg atgtcggata caattgtgat tataaggctt ttgatggcct   180
aattacggag caaattttga gtctcgagac cggagcggcc ctggcaattt ggcaaagagt   240
gccgcagctc tcgactcctc ccgtagccgg gtgagccttt ccacaatggc cgaacaaac    300 tcggaccggg ttggtgcaaa agccccaaca gccctaaagt agggagctgg ggtccggatg   360
atagaaacgt tgatcttcct caacatgagg ctgagcccag actgtgctca accgtgagag   420
ggctagccgg cagaggagta atctacattc ccaaggattg ccaggcaaat agatacttgg   480
gcaccctgaa atacgtgat atgatctcag acttcaaggg atcc                     524
```

<210> SEQ ID NO 25
<211> LENGTH: 1620
<212> TYPE: DNA
<213> ORGANISM: Artificial Sequence
<220> FEATURE:
<223> OTHER INFORMATION: Synthetic Construct

<400> SEQUENCE: 25

```
ggatccggta cccgatgaat tgtgctttcc atatcctgat cctaagcagc ccgccatcct     60
tagcgcagag gatgaacgcc ttaagggaac gatccatgaa ggatacactc cgttaaggga    120
```

-continued

```
tggcatgaag aagtttgctg agccaatgta tctgctagag gaaaaactac tcgatgaagt    180
tgcaggtgac atggttcaga cgtggtatga ctcgaccttg ttgagagtaa aattttgtc    240 tttttcccgc ctactgatga agaagagagg ccacctgcct tgtcaagtgg gcatcaatcc    300
ttatagtcgc gaatgaccg atttgtatca ccgcttaggt gaactcctg atgtcggata     360 caattgtgat tataaggctt ttgatggcct aattacggag caaattttga gtctcgacta    420
cctatggtga tgataatgtc ttcactgtgg cacaatctgt catgcagtac tttactggcg    480
atgctctgaa aatgcaaatg gcaaagcttg gggtaactat tactgatggg aagataagt     540 ctctttccac tattccagcc cgtccactgc tggaattaga gttttttgaaa cgtggatttg    600 ttagaagctc tgggggtatg ataaatgcgc ctttggaaaa attatcaata atgagttctt    660
tggtctacat cagaagtgat ggctcagaca tgttgcagaa actattggac aatgttaata    720
ctgcacttgt cgagctttat ctacatggtg actcgggacc ggcgggccct tagtgagtgg    780
aacgggacca ctatgactg gaatgaactt tttaagtatc ccggggtgta tgtggaagag     840
gacggaagtt ttgaagtaaa gattcgctct ccatatcacc gaactcctgc cagattgctt    900
gctggtcaaa gtcaggcggc ccagaagaaa ttgagattgg ttctcgtttc ttcgatttca    960
cttcgaatac ttgtagggta tctatgggtg aaaatccgtt tgctgcaatg attgcctgcc    1020
atggattgca tagtggtgcg gcccttagc ttttatggta gaaccagttt cccagtctag     1080
tgatacgtag atatctaggg tatctggctt taaaagaccc aagtgtatat atgtgttttg    1140
tcagtagcat gtattatctt tgttataat ttgttttaac ttgttttccg cttttgtgtg     1200
tttagtttca tgctttagt ggcgacagtg tgttgtttgt cctttggaca cacttgccta    1260
gttggacgca aaaagatttt tccttttcttt ttactggcgg ccgctccgga ccccagctcc    1320
ctactttagg gctgttgggg cttttgcacc aacccggtcc gagtttgttc gggccattgt    1380
ggaaaggctc acccggctac gggaggagtc gagagctgcg gcactctttg ccgaattgcc    1440
agggccgctc cggatgatag aaacgttgat cttcctcaac ttgaggctga gcccagactg    1500
agctcaaccg tgagagggct agccggcaga ggagtaatct acattcccaa ggattgccag    1560
gcaaatagat acttgggcgc cctgaatata cgtgatatga tctcagactt caagggatcc    1620
```

<210> SEQ ID NO 26
<211> LENGTH: 1247
<212> TYPE: DNA
<213> ORGANISM: Artificial Sequence
<220> FEATURE:
<223> OTHER INFORMATION: Synthetic Construct

<400> SEQUENCE: 26

```
ggatcccagt aaaagaaag gaaaaatctt tttgcgtcca actaggcaag tgtgtccaaa      60
ggacaaacaa cacactgtcg ccactaaaag catgaaacta acacacaaa agcggaaaac     120 aagttaaaac aaattataac acaaaataat acctgctact gacaaaacac atatatacac    180
ttgggtcttt taagtcagat accctagata tctacgtatc actagactgg gaaactggtt    240
ctaccataaa agctaaaggg ccgcctgact ttgaccagca agcaatctgg caggagttcg    300
gtgatatgga gagcgaatct ttacttcaaa acttccgtcc tcttccacat acaccccggg    360
atacttaaaa agttcattcc agtccatagt ggtcccgttc cactcactaa gggccgccg    420 gtctcgagtc ataccacgtc tgaaccatgt cacctgcaac ttcatcgagt agttttttcct    480 ctagcagata cattggctca gcaaacttct tcatgccatc ccttaacgga gtgtatcctt    540
catggatcgt tcccttaagg cgttcatcct ctgcgctaag gatggcgggc tgcttaggat    600
```

```
cccttgaagt ctgagatcat atcacgtata ttcagggtgc ccaagtatct atttgcctgg      660
caatccttgg gaatgtagat tactcctctg ccggctagcc ctctcacggt tgagctcagt      720
ctgggctcag tctcaagttg aggaagatca acgtttctat catccggagc ggccgcacca      780
ctatgcaatc catggcaggc aatcattgca gcaaacggat tttcacccat agatacccta      840
caagtattcg aagtgaaatc gaagaaacga gaaccaatct caatttcttc tgggcccgcc      900
ggtctcgagt caccatgtag ataaagctcg acaagtgcag tattaacatt gtccaatagt      960
ttctgcaaca tgtctgagcc atcacttctg atgtagacca agaattcat  tattgataat     1020 ttttccaaag gcgcatttat catacccca  gagcttctaa caaatccacg tttcaaaaac     1080
tctaattcca gcagtggacg ggctggaata gtggaaaggg acttatctct cccatcagta     1140
atagttaccc caagctttgc catttgcatt ttcagagcat cgccagtaaa atactgcaga     1200
cagattgtgc cacagtgaag acattatcat caccataggt aggatcc                   1247

<210> SEQ ID NO 27
<211> LENGTH: 7342
<212> TYPE: DNA
<213> ORGANISM: Artificial Sequence
<220> FEATURE:
<223> OTHER INFORMATION: Synthetic Construct

<400> SEQUENCE: 27
atgaaaattt cccacaagtt cttacgttac cgtgattgca atcttttcct gtgaagagtt       60
taagaaactc aagattgaaa tcctttgcga agagtttaag aaactcaccc ctcgaagcgt      120
ttaagaaacg cattgtttta ttgtgcttgt tgcttatttt gtgcagttta cttttaatct      180
acatatttta ctgtgttatt tatttaagtt taattttgta gttgtaaaag ttgtttgcca      240
ctatgtggca ggtgcctgag ggctcccagt gctgctgcac tgggaagtcc ttttcaaacg      300
cggaggctaa ggaactccgc tacgtgtgct catgttggat gagcacacgt cttgttaagg      360
ctgaggctcc tcctcagcaa tcaaggaaga gtgggatagc gcccactccc ctaaaatcca      420
aagggaccat tcaggtctca ctcccaaagg ctactgggt  caaacccagt atccataaat      480
ccaaaggagc ttctgtggct cctgcacctt tgcttaagca aaggtgtgaa gtagtcgttc      540
aatatgggcc tcctgccgat attgaattgg tctacccgcc tcttgtgcgg gaggaggaga      600
agtcctccaa tatagtggtt ctgccaccta cccaaaaggt ggaagtaagg gtgccagttt      660
gctgtgcacc caagtggatg gtggctatcc ctaagccacc ggtgaagcta gcccctaaag      720
ctagcaagct acggtttcct aaaggagccg tagcttacaa tggtgtcaat tttattgaca      780
ctaaggggaa agtcgtccta tctgagggcg caaagaggat ccttagggg  atccgcgttg      840 ctgcaaagca acgtcttcgt gctgcgcgca ggtctgctgc gtgcaagaag gtgagggcca      900
agcgtgctct tgccgagttt gaggcaatcg ttcaaagtga acgattggac cagttaaaga      960
ctgggttcca agtggtgctt ccagcaccaa agatgagctg cagcttaaaa gaagctgctc     1020
cttctaccac ttctgtggtg gtagttaaga gaggaagct  gccaaggctt cctaaaattc     1080
tgcctgagca ggacttctcc tgcttagagg ctttgactg  ggggagaaa  tcccacccag     1140 ttgaggtaga catcgaggat gattggatcc tcgtggaaaa acctgtcctt aagagacagg     1200
ctgtgcaaac tgcacagggc agggcaaccg aggccttaac tcggtttgca gctaccagtg     1260
gcttctcact gggcgcccac caaaaggtgg aagatttcgc ttcgtctggt gaagcggaat     1320
atttgatggc aggagagttt gcagacctct gcttgctatc tttggtgtat aatgatgcac     1380
cgacgttgtc tgcgactatt gaggaactca gggatagcaa agattttcta gaggctatcg     1440
```

```
aactcctcaa gttggaatta gctgaaattc aacagactc cactacatgt gccccattta   1500
aacaatgggc ttctgctgcc aagcagatgg ctaaaggggt tggcactatg gttgggatt   1560 ttactagagc tgctggagcc gctgtcgtta tctcttttga tatggcagtg gaatttctgc   1620
aagataaagc gttaaagttc tgtaaaagaa tctttgacgt aacaatggct ccatatctcc   1680
agcatcttgc cagtgcacat tccatcctta agaagatttg ggaaaaattg tcagaatgga   1740
tggaaagcct caagagtaaa gctagtttag cacttgaagt aatgcggcaa cacgccattt   1800
tcgctttagg tgctatggtt ataggagtg tagtagtgtt ggtagaaaaa gtgcttattg   1860
cagccaaaat tatccctaat tgtgggatta ttctgggtgc cttttgaca cttttctttg   1920 ctagcctggg gttaacagcc ctggagtgca ctgcagagga aatcttcaga atgcatgcgt   1980
gttgtaaaag tgctatttac tccatgtatt ctgttgcaga gcctactatg gctgatgagg   2040
gagaatctca cactatgggg gcgactcagg gacttgataa tgcaattcag gccctgactc   2100
gagtaggaca gagtatgata agcttcaaac tggggagctt ttcatattat gcaaagatag   2160
cccaggggtt tgaccaactt gcaaggggta agcgagcaat aggtgaactt actagttggc   2220
tcatcgatct tgttggaagt atttactccc aggtttctgg acaggaaagt acttttttg    2280 acgagctttc tacaattgtt tgcctagatg tgagagcatg gctactgaaa agtaagcgtg   2340
ttcggttgca agtggaaaca atggccatag gcgatagaat aaccttggat actattgcca   2400
aattgttaga agaaggccac aagatactgg tcactgcggc aggtgttcca aggaaaacgt   2460
ctgctgattt tacaatgtgc atcaaggaag aagtgtctaa gttggaagaa gtgcatgcca   2520
gaacggcatg tgcgggaatc aatgagggta tgcgagcttt tccttttgg gtgtacattt    2580 ttggtgcttc acagtctggg aagacaacaa tagcaaattc aatcattatt ccagctttgc   2640
tggaagaaat gaatcttccc aagagctcag tttattccag gcccaagact ggtgggtttt   2700
ggagtggtta tgctaggcaa gcatgtgtga agttgacga tttttatgca attgagcaga    2760
cccctagcct ggcgagttct atgattgatg tggtgaattc agaaccttat cccctcgaca   2820
tggcttacat tcacgagaag ggaatgtcaa tggattctcc attagttgta accactgcaa   2880
ataccgccgt gcctcctacc aattctcagg tggtggactt gccgtcattt tataacagga   2940
gggcggcggt actggaagta cgcaggaagg atgggagttt ctttacaccg cgggcgtatg   3000
attcatgcat tgaagttcgc ttcatgcata taagtgtcc gtatgttgat tctgctgggg    3060
tgcctcaggg ccctgcagta aacactccca tggatgaagg atggatcact ccaagtgagg   3120
ctgttgcagt tctcaaaaat ctcttgggtg aacacatttt ggctgaggaa gcaaagctgc   3180
tggaatacag agagcggatt ggtaatgacc atcccatata taacgcagca aaggaattca   3240
taggcaacat gcactatcct gggcagtggc tgactgctga acagaagagt acctatggaa   3300
tcaaggatga tggattctct ttccttgcgg ttgatggaaa gatatacaag tacaatgtac   3360
tgggtaagtt gaatccatgt gagtctgaac caccacatcc caatgtgatt ccatggttgg   3420
aaagaaaaac attagaaatt gtacattggg atgtgcataa acatattgcc actggtcccc   3480
gcaatgcact ggttgcatgc tttttgcagg gcttggtcca aggacaaagc aaagtagaga   3540
gtgtggaacg tatggggaaa gatagttctc cggaacaaca gaattttttt aaacgcttga   3600
gtttatccga gagaatttat ctgaggctgt gccaaatccg cattgataat atccagaaag   3660
aagagctggc gggttctggt agagggccca tggcaatatt gagagagtgt ctgatgaaga   3720
gtaagcaggt agtggtggaa aactactcat tgcattgac attggtggct attctcttgc    3780
ttatcagtgc tgcttacacg ctactctcaa cagtggtggc tctggcgggt tgctctagtt   3840
```

```
ttgctggtgg tatggttgca gtgacggctg tcaacaatgc ttctataccg tgttcagagc    3900
ctcgcttgga ggaaagatat tcccctagaa atcgttttgt ctcgcgaatt tctaaaatta    3960
ggggtgaggg accttccaaa ggacaaggtg agcatgagga attggttact gagctctatt    4020
actattgtga tggagttaag aagctaattt ccacgtgttg gtttaaggga aggtcactct    4080
tgatgacgag acatcaagcc ctggccgttc cgatcggcaa tgaaattgaa gtaatatacg    4140
ctgacggaac aacaaaaaag ttagtttggc caggcaggca ggaggatggc aattgcaaag    4200
gcttcgtcga attccctgaa aatgagttag ttgtctttga gcatccacac ttattgacac    4260
tgcccattaa gtatgagaag tactttgttg atgatgccga tagacagatt tcccccaacg    4320
ttgcggttaa gtgttgcgtt gcgcgcttag aagatggaat tccccaattc cacttttgga    4380
gcaaatatgc aacagcccgc agtgaagttc atacgctgaa agatgagggc ggggaaatg     4440 tctaccagaa caagataagg cgctatattg tttatgcgca tgaagcaaag aagtatgatt    4500
gtggagcctt ggctgtggct gtgatccaag gaatcccaaa agtcatcgca atgcttgttt    4560
ctgggaatag aggtgtgacc tactcttctg tgattccaaa ctacagttct tcttttatta    4620
ggggagaagt gccatatgta ccagaagatg ggttagtgtc gagggatat aggaaagtgg     4680 gttatttgca cgcatcggat gcgccacatg tgccttctaa gacttccttc atgaaggtac    4740
cagatgaatt gtgcttttcca tatcctgatc ctaagcagcc cgccatcctt agcgcagagg   4800
atgaacgcct taagggaacg atccatgaag gatacactcc gttaagggat ggcatgaaga    4860
agtttgctga gccaatgtat ctgctagagg aaaaactact cgatgaagtt gcaggtgaca    4920
tggttcagac gtggtatgac ccgggtgaat tccttgaaga tatttcttta gatcaagcta    4980
tcaatgggga catggatgag gaatattttg acccccctagt gatggacacg tctgaaggat   5040
atcccgatgt tttagatcgt aaacctgggg aaaagggaaa ggcgagattc tttgttgggg   5100
aaccaggaaa tagagccttt gtagctggtt gtaatcctga aaaggcttat taccaactag    5160
aagaggactc taaaaccaag ataccttcct tggttagtat agaaacccca aaagacgaga    5220
gattaaaaag aagtaaaatc gatactcctg gtacgagatt attttctgtg ctgcccttgg    5280
catataatct cttgttgaga gtaaaatttt tgtctttttc ccgcctactg atgaagaaga    5340
gaggccacct gccttgtcaa gtgggcatca atccttatag tcgcgaatgg accgatttgt    5400
atcaccgctt aggtgaactc tctgatgtcg gatacaattg tgattataag gcttttgatg    5460
gcctaattac ggagcaaatt ttgagtacga tcgccgatat gatcaatgct ggatatcgtg    5520
accctgtcgg caataggcag aggaaaaatt tgctcctagc aatatgtgga cgcctctcta    5580
tctgtggaaa tcaagtgtat gccactgaag caggcatacc ttcaggctgt gctctcacag    5640
tagtactcaa ttccattttt aaagaactac tgatgagata ttgcttcaag aaaatagttc    5700 ccctgtgta caaggaatgt tttgacagat gtgtcgtgct cattacctat ggtgatgata    5760
atgtcttcac tgtggcacaa tctgtcatgc agtattttac tggcgatgct ctgaaaatgc    5820
aaatggcaaa gcttggggta actattactg atgggaaaga taagtctctt tccactattc    5880
cagcccgtcc actgctggaa ttagagtttt tgaaacgtgg atttgttaga agctctgggg    5940
gtatgataaa tgcgcctttg gaaaaattat caataatgag ttctttggtc tacatcagaa    6000
gtgatggctc agacatgttg cagaaactat ggacaatgt taatactgca cttgtcgagc    6060
tttatctaca tggtgataga acttattttg aatcagtcag agcttttttac ttcgagaaac    6120 tccctcctgg cgcttataag gagttgacaa cgtggtttca agcagaatca tttcatgagt    6180
gtcagaagag tggagagagt ggttataagc cacaagggct cattgagatt agtcatggag    6240
```

```
cagcttttgc cagttttact caacaagctg gtacagagtt ggaaaagcat gacatttgcc    6300
ctggcttatc gattgcagga actaagtaca ttgctactga gaatgagatt gttttgtctc    6360
ttagttccgt cctacccggg gatagaaatg ttttcaagtt ggatctgcct tgtggagacg    6420
ggatagggcg tttgccttcc aaatgcagta tcttaaactt gagaaaaccg ggcttggtta    6480
tgagattgtg caagcgtgcc caagatgaaa agaagacctt agttattcgt gacgaaaggc    6540
catacattgg tgcatgggca gttgcttgca tatgtggaga gagttttggc ttcgggcaac    6600
agagcgttct tgcgctttat gccaacttgt tgggaccaaa tcagaggaat ggcttagcca    6660 gttattttc tgattttgaa agtcccattc atatcaagaa agtccatgcc aaaacaaact    6720
cttatgaggg gggtgaagct ttaaaggaaa ttttcacttt tgtgagact attttctatg    6780 aagccaccga aatggatact aggaaagtga tgttgcaaaa tcaaccagac gtctatccta    6840
gtataagtct tgttgggggg gtttgtttcc caaatgaggg aggagagcct ggagccatgt    6900
actcggaaac agatgttacg atggctagag aggttcaagg agtctatgta agtgaagcgt    6960
gcgtgaaatg ttgcaggcgt tgtgtaggag tagcaaccag ggttgtgact gatacgcaac    7020
tttttggcaa caatctttta aagactcatc ttaaggcttt gaggaaaatt cagaatcata    7080
catgccttag gaaataagcc ttccaattct tggtactggg ataaccaagt ttaaataacc    7140
cagtttcttt tgcctttcat gctcttttag gcaattgaat attagagcat ttgtgttatt    7200
gtttgtttta acttgttttc tgcttagtg tgttttcttt catgctttta gtggcgacag    7260
tgtgttgttt gtcctttgga accacttgcc ttgttggacg caaaaagatt ttctttttc    7320 ttttactgt tatgcaaatt tt                                              7342

<210> SEQ ID NO 28
<211> LENGTH: 3774
<212> TYPE: DNA
<213> ORGANISM: Artificial Sequence
<220> FEATURE:
<223> OTHER INFORMATION: Synthetic Construct

<400> SEQUENCE: 28
atgaaaaatg tttacgtttt cttacgttac cgtgatttca cttttcttta gccaagagtt     60
taagaaactc aaaagtgaaa ctgccaagag tttaagaaac tcacaaagcg aagagtttaa    120
gaaactcatc attgcttttt tgttcttttta ttttgcgctt tatttgttta gcattttatt    180
tagttctttt aaaaagcttt tgttttgttt ttcttttct ttacttgccc ttatgggcaa     240 atttattat tccaacaggc ggcttgcctg ttgggctgct gggaagaacc ctcatcttgg     300
gggttctgtt gaacaatggc tggcggccat taacactgat ccctccttcc gccaaactgt    360
taaggaggat gtccaagaaa accgagaaca gccaactgct gttcgaatgt tttcttggaa    420
agttgggtcc gggcccattg acaatcccga gaaatgcgac tggcatttttg tccttacggg    480 cgagaggcca gcgccgtccc ggccggttaa agccgatgag gttgtggtgg tgccacaacc    540
gaagaaggtg gtgattccaa caccacctcc tccccagct ccctacttta gggctgttgg    600
ggcttttgca ccaacccgt ccgagttgt tcggccatt gtggaaaggc tcacccggct    660
acgggaggag tcgagagctg cggcactctt tgccgaattg ccattggagt accctcaggg    720
tgctcctctg aagttgagcc tggcggcgaa attcgccatg ctcaaacata ccacttggag    780
gaagtggtat gacactagtg atgagcgcct tttggaggct catcctggtg gtccttgtct    840
tcctccccct ccccaatcc aaaatcctcc ctccttccag gagagggtga gggagttttg    900
caggatgaag tcctgcacca aggctttcgc cttggaaacc tccctaggtc tcaataaggc    960
```

```
ctgggtaggt ttagtggaca tccccagtac ttctgtgtgc tgtgcggatg ggaagactac    1020
cggtgggcag acaattgccc aggaagctga tcctttgcaa cataggatca gtacgtcagt    1080
agcccccggt agggcacaat ggatctccga gcgcagacaa gctctgcgga ggagagagca    1140
agcaaatagc ttcgaaggtc ttgctgctca aaccgatatg acttttgagc aggccaggaa    1200
tgcttatctt ggtgctgccg acatgattga gcaaggccta ccgctgcttc ccctctgcg    1260 cagcgcttac gccctaggg gtttgtggag gggaccctca accagagcca attacacgct    1320 agatttagg ctcaatggta ttccgaccgg gacaaacaca ttggaaatat tgtataatcc    1380
tgtgtcggag gaagagatgg aagagtaccg ggacaggggc atgtcagctg tggtaattga    1440
tgcgctagaa atagccataa acccatttgg catgcctgga aatcctacgg acttgactgt    1500
cgtagcgaca tatgggcatg agcgcgacat gacgcgcgcc tttattggat ctgcttccac    1560
attcttaggg aatgggttag ctagagccat tttctttcct ggtttgcaat atagccagga    1620
ggaaccaagg cgcgaatcta taattcgcct atatgttgcc tctaccaatg ccactgtgga    1680
tactgattca gtcttggcag ccattagtgt tggcactttg cgtcaacatg ttggttccat    1740
gcactaccgg acagtggcta gtaccgtgca ccaggctcag gtgcaaggaa cgacgctcag    1800
ggctactatg atgggtaaca ctgtcgtagt atcacctgaa ggaagcctgg ttactggaac    1860
ccctgaagca agagttgaaa taggggggcgg ttctagtatt aggatggtgg gacctctaca    1920
gtgggaaagt gtggaggaac cagggcaaac cttctctatc agaagccgtt cacggtctgt    1980
gaggattgat agaaacgttg atcttcctca acttgaggct gagcccagac tgagctcaac    2040
cgtgagagga ttagctggta gaggagtaat ctacattccc aaggattgcc aggcaaatag    2100
atacttgggc accctgaata tacgtgatat gatctcagac ttcaagggtg tccagtatga    2160
aaagtggata actgcaggat tagtcatgcc tactttcaag atagttatta ggctacctgc    2220
aaatgccttt actggattga catgggtgat gagctttgat gcttataacc ggataactag    2280
tagaattact gctagtgcgg atcctgtata caccttgtca gtcccacatt ggcttatcca    2340
ccataagttg ggcacgtttt catgtgagat agactatgga gaattgtgtg gtcatgctat    2400
gtggtttaaa tcaaccacat ttgaatctcc aaggttgcat ttcacgtgtt taacgggcaa    2460
caacaaagag ttagcggcag actggcaagc tgtcgtagaa ctatatgccg aattggaaga    2520
ggccacttct ttccttggga aaccaacttt ggttttgac ccaggtgttt tcaatggcaa    2580
atttcaattt cttacttgcc ctcccatatt ctttgattta acggccgtca cggcccttag    2640
gagtgctggg ctgacattgg ggcaagtccc aatggttggc accactaagg tttataatct    2700
aaacagcact cttgtgagtt gtgttttggg tatgggaggt actgttagag ggagggtgca    2760
catttgtgcg ccaatcttct acagtattgt tttatgggtc gttagtgagt ggaacgggac    2820
cactatggac tggaatgaac ttttttaagta tcccggggtg tatgtggaag aggacggaag    2880
ttttgaagta aagattcgct ctccatatca ccgaactcct gccagattgc ttgctggtca    2940
aagtcagaga gacatgagct ctcttaattt ttatgcaata gcaggaccta tcgctccttc    3000
gggtgagact gcgcaacttc ctattgttgt gcagatagat gaaattgtgc gcccagatct    3060
ctctttacca agttttgaag atgactattt cgtatgggtg gattttctg aattcactct    3120 tgataaagaa gaaattgaga ttggttctcg tttcttcgat ttcacttcga atacttgtag    3180
ggtatctatg ggtgaaaatc cgtttgctgc aatgattgcc tgccatggat tgcatagtgg    3240
tgtattagac ctcaaactcc aatggagtct gaacaccgaa ttcggcaaga gcagcgggag    3300
cgttaccatc acgaagctgg tgggtgataa ggccatgggt ctggacggac cttctcacgt    3360
```

-continued

| | | | | | |
|---|---|---|---|---|---|
| ttttgccata | caaaaactag | agggaactac | agagttgttg | gttgggaatt | ttgcaggagc | 3420
| aaacccaaac | actcgttttt | ccctttatag | tcgctggatg | gcaattaaat | tggatcaagc | 3480
| aaagagtatt | aaagtactcc | gcgttttgtg | caagcccgt | ccaggcttta | gcttttatgg | 3540
| tagaaccagt | ttcccagtct | agggtatctg | actttaaaag | acccaagtgt | atatatgtgt | 3600
| tttgtcagta | gcatgtatta | ttttgtgtta | taatttgttt | taacttgttt | tccgcttttg | 3660
| tgtgtttagt | ttcatgcttt | tagtggcgac | agtgtgttgt | ttgtcctttg | gacacacttg | 3720
| cctagttgga | cgcaaaaaga | tttttccttt | cttttactg | ttttgcaaat | ttat | 3774